(12) United States Patent
Holt et al.

(10) Patent No.: US 9,662,271 B2
(45) Date of Patent: May 30, 2017

(54) VIAL ADAPTER AND SYSTEM

(75) Inventors: Mark Dominis Holt, Moorpark, CA (US); Alexander Stuart Cairns, Santa Monica, CA (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 13/503,508

(22) PCT Filed: Oct. 22, 2010

(86) PCT No.: PCT/US2010/053864
§ 371 (c)(1),
(2), (4) Date: Aug. 2, 2012

(87) PCT Pub. No.: WO2011/050333
PCT Pub. Date: Apr. 28, 2011

(65) Prior Publication Data
US 2012/0296307 A1     Nov. 22, 2012

Related U.S. Application Data

(60) Provisional application No. 61/254,520, filed on Oct. 23, 2009.

(51) Int. Cl.
*A61B 19/00* (2006.01)
*A61J 1/20* (2006.01)
(Continued)

(52) U.S. Cl.
CPC ........... *A61J 1/2096* (2013.01); *A61J 1/2089* (2013.01); *A61J 1/201* (2015.05); *A61J 1/2051* (2015.05);
(Continued)

(58) Field of Classification Search
CPC .. A61J 1/2096; A61J 1/2089; A61J 2001/201; A61J 2001/2055;
(Continued)

(56) References Cited

U.S. PATENT DOCUMENTS

| 3,977,555 A | 8/1976 | Larson |
| 4,614,437 A | 9/1986 | Buehler |

(Continued)

FOREIGN PATENT DOCUMENTS

| EP | 1150639 A1 | 11/2001 |
| EP | 1323403 | 7/2003 |

(Continued)

OTHER PUBLICATIONS

Supplementary European Search Report, European patent application No. EP 10825791, dated Mar. 3, 2015.
(Continued)

*Primary Examiner* — Tatyana Zalukaeva
*Assistant Examiner* — Andrew J Mensh
(74) *Attorney, Agent, or Firm* — Marshall, Gerstein & Borun LLP

(57) ABSTRACT

A vial adapter includes a base having first and second opposing sides, a spike depending from the first side of the base, the spike having a spike passageway, and a connector disposed on the second side of the base, the connector having a connector passageway that is in fluid communication with the spike passageway. The vial adapter may be combined with a vial.

10 Claims, 26 Drawing Sheets

(51) Int. Cl.
*A61M 5/32* (2006.01)
*A61M 5/158* (2006.01)
*A61M 1/14* (2006.01)

(52) U.S. Cl.
CPC .............. *A61J 1/2055* (2015.05); *A61M 1/14* (2013.01); *A61M 2005/1581* (2013.01); *Y10S 604/905* (2013.01)

(58) Field of Classification Search
CPC ...... A61J 2001/2013; A61J 2001/2058; A61M 2005/1581; A61M 2025/078; A61M 33/1011; Y10S 604/905
USPC .......................................... 604/407, 411, 414
See application file for complete search history.

(56) References Cited

U.S. PATENT DOCUMENTS

| | | | |
|---|---|---|---|
| 4,675,020 A | | 6/1987 | McPhee |
| 4,677,980 A | * | 7/1987 | Reilly et al. ................ 600/432 |
| 4,759,756 A | | 7/1988 | Forman et al. |
| 4,936,841 A | | 6/1990 | Aoki et al. |
| 4,940,460 A | | 7/1990 | Casey et al. |
| 5,100,394 A | | 3/1992 | Dudar et al. |
| 5,171,214 A | | 12/1992 | Kolber et al. |
| 5,195,992 A | | 3/1993 | Dudar et al. |
| 5,250,037 A | * | 10/1993 | Bitdinger ................ 604/192 |
| 5,270,219 A | | 12/1993 | DeCastro et al. |
| 5,279,576 A | * | 1/1994 | Loo et al. .................. 604/187 |
| 5,334,179 A | | 8/1994 | Poli et al. |
| 5,429,614 A | | 7/1995 | Fowles et al. |
| 5,445,631 A | | 8/1995 | Uchida |
| 5,466,220 A | | 11/1995 | Brenneman |
| 5,526,853 A | | 6/1996 | McPhee et al. |
| 5,647,845 A | | 7/1997 | Haber et al. |
| 5,649,912 A | | 7/1997 | Peterson |
| 5,893,397 A | | 4/1999 | Peterson et al. |
| 5,931,794 A | * | 8/1999 | Pitesky ........................ 600/556 |
| 5,957,898 A | * | 9/1999 | Jepson et al. ................ 604/256 |
| 6,071,270 A | | 6/2000 | Fowles et al. |
| 6,090,091 A | | 7/2000 | Fowles et al. |
| 6,120,490 A | | 9/2000 | Neftel |
| 6,209,738 B1 | | 4/2001 | Jansen et al. |
| 6,319,224 B1 | | 11/2001 | Stout et al. |
| 6,358,236 B1 | | 3/2002 | DeFoggi et al. |
| 6,474,375 B2 | | 11/2002 | Spero et al. |
| 6,656,433 B2 | | 12/2003 | Sasso |
| 6,755,810 B1 | | 6/2004 | Buch-Rasmussen et al. |
| 6,875,205 B2 | | 4/2005 | Leinsing |
| 6,890,328 B2 | | 5/2005 | Fowles et al. |
| 7,140,401 B2 | | 11/2006 | Wilcox et al. |
| 7,326,194 B2 | | 2/2008 | Zinger et al. |
| 7,354,427 B2 | | 4/2008 | Fangrow |
| 7,425,209 B2 | | 9/2008 | Fowles et al. |
| 7,452,348 B2 | | 11/2008 | Hasegawa |
| 7,473,246 B2 | | 1/2009 | Vancaillie et al. |
| 2002/0068896 A1 | * | 6/2002 | Robinson et al. ............. 604/82 |
| 2002/0173748 A1 | * | 11/2002 | McConnell ........... A61J 1/2096 604/167.02 |
| 2003/0079314 A1 | | 5/2003 | Yeh |
| 2004/0210207 A1 | * | 10/2004 | Amisar ................. A61J 1/1412 604/415 |
| 2004/0236305 A1 | * | 11/2004 | Jansen et al. ................. 604/411 |
| 2005/0148994 A1 | | 7/2005 | Leinsing |
| 2006/0025747 A1 | | 2/2006 | Sullivan et al. |
| 2006/0259004 A1 | | 11/2006 | Connell et al. |
| 2007/0060904 A1 | * | 3/2007 | Vedrine et al. ............... 604/411 |
| 2007/0088315 A1 | | 4/2007 | Haindl |
| 2008/0300536 A1 | * | 12/2008 | Wang .................... A61J 1/2089 604/89 |
| 2009/0036764 A1 | * | 2/2009 | Rivas et al. ................. 600/365 |
| 2009/0093757 A1 | | 4/2009 | Tennican |
| 2011/0004187 A1 | * | 1/2011 | Beiriger ....................... 604/500 |
| 2012/0067429 A1 | * | 3/2012 | Mosler et al. .................... 137/1 |

FOREIGN PATENT DOCUMENTS

| | | |
|---|---|---|
| WO | WO 95/05211 | 2/1995 |
| WO | WO 02/102704 | 12/2002 |
| WO | WO 03/082398 | 10/2003 |
| WO | WO 2005/086587 | 9/2005 |
| WO | WO 2006/124756 | 11/2006 |
| WO | WO 2008/093063 | 8/2008 |
| WO | WO 2010/096061 | 8/2010 |
| WO | WO-2011/039747 A1 | 4/2011 |
| WO | WO-2012/020083 A1 | 2/2012 |

OTHER PUBLICATIONS

Supplementary Partial European Search Report. European Application No. EP 10825791, Nov. 21, 2014.

\* cited by examiner

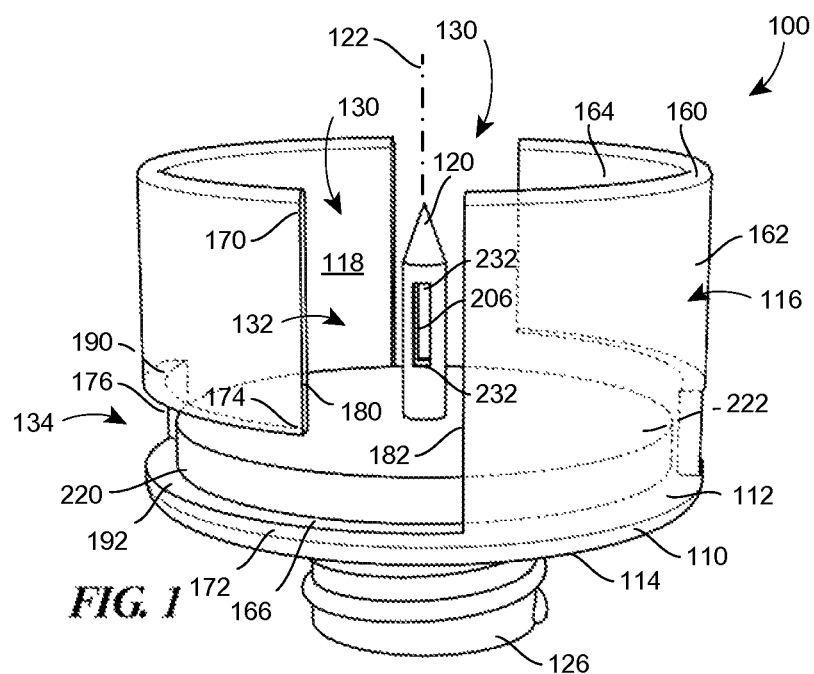
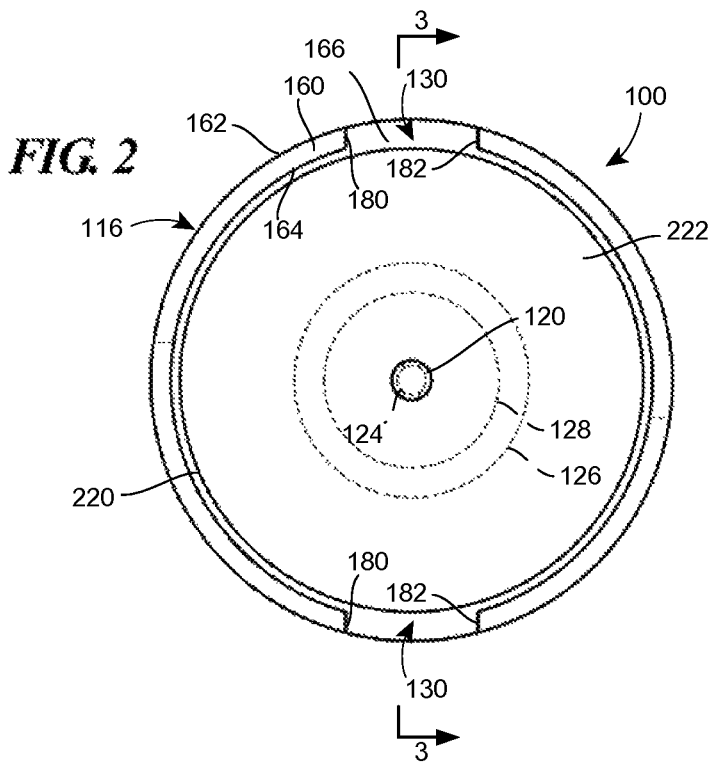

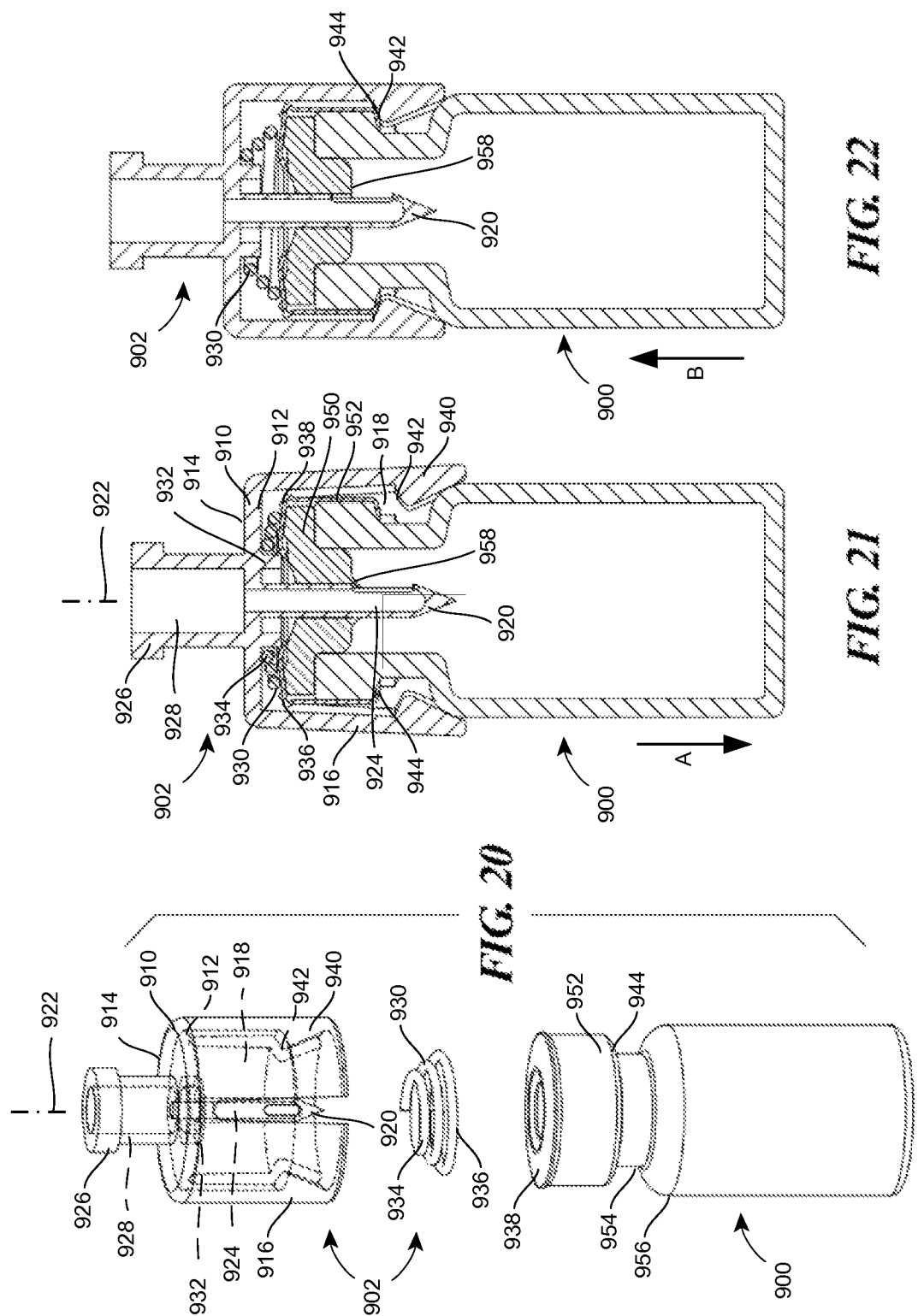

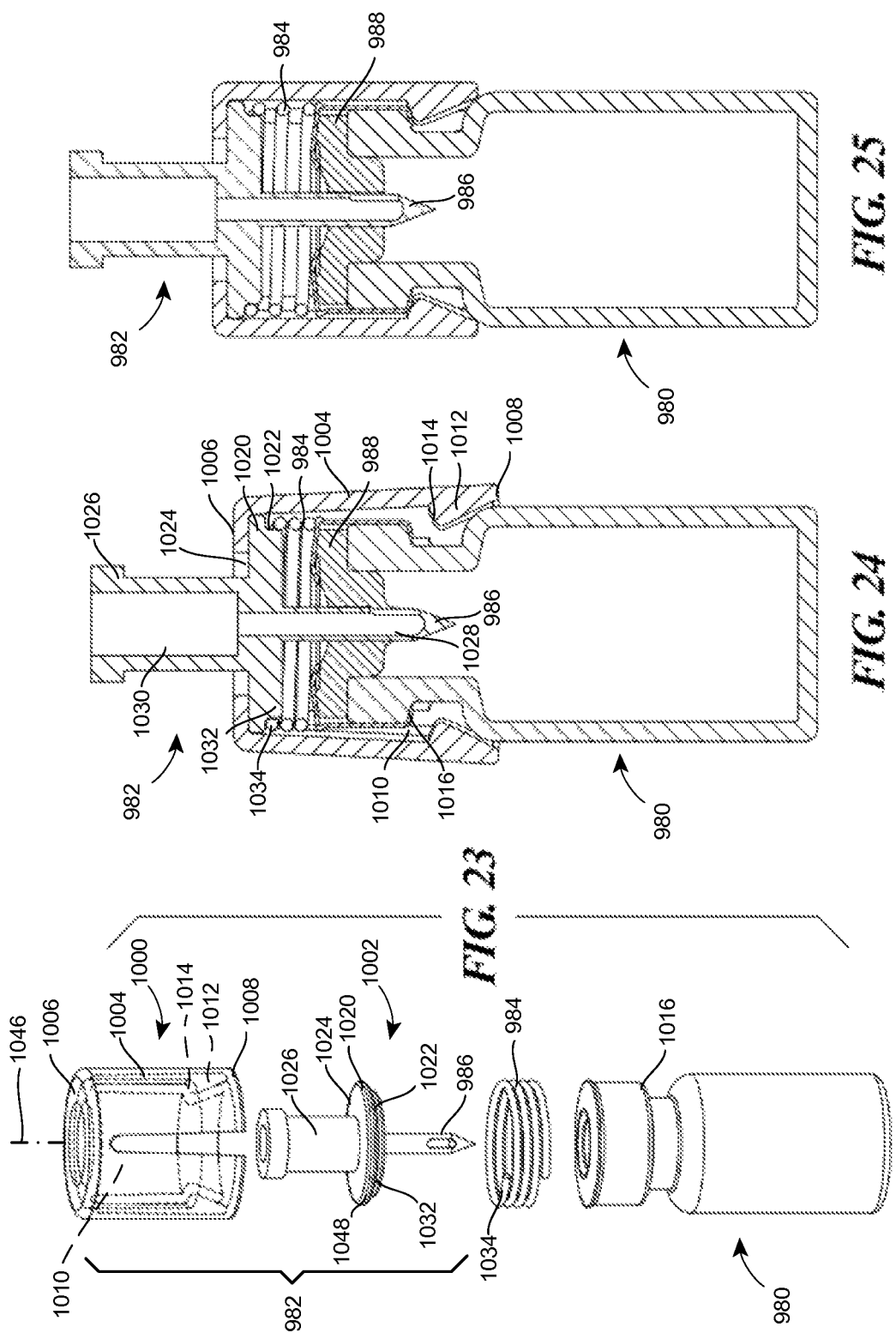

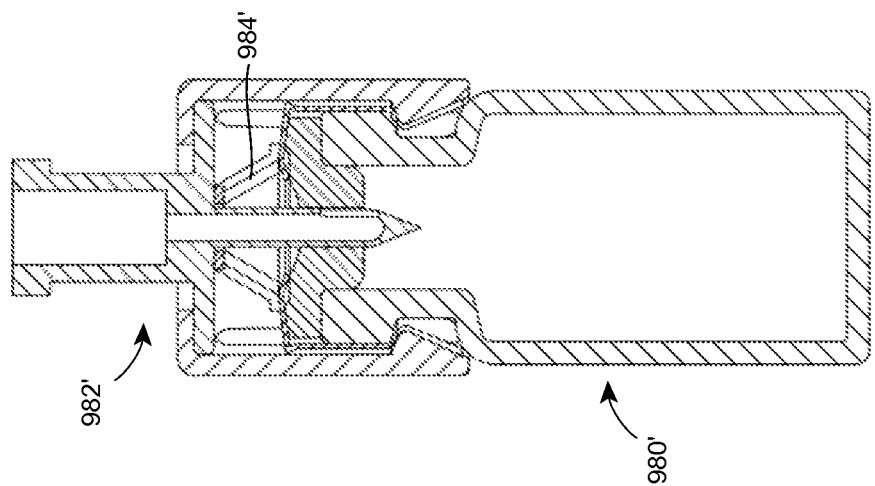
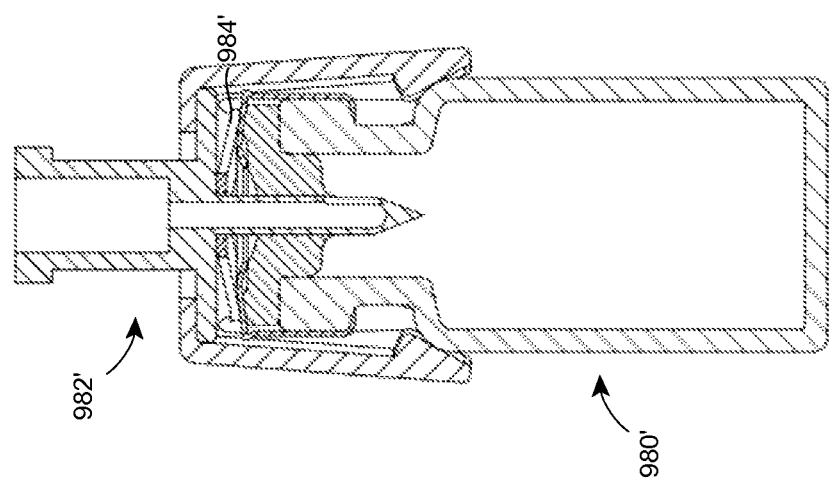

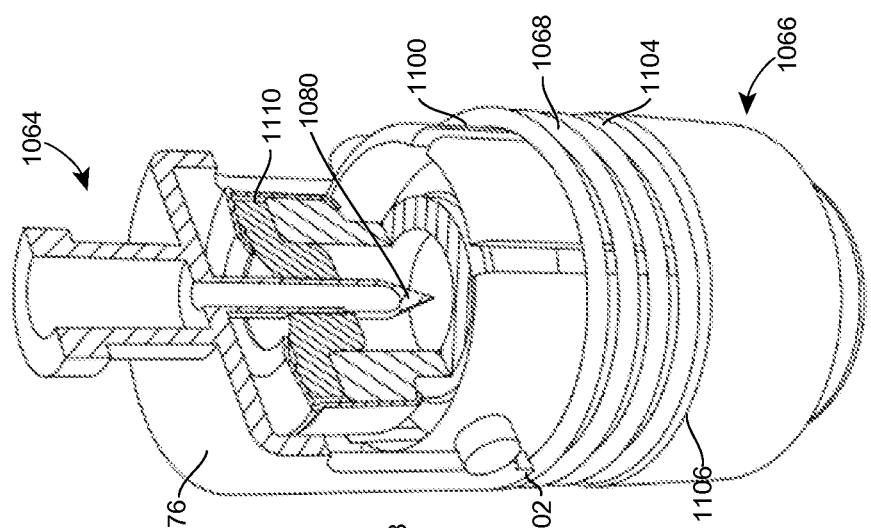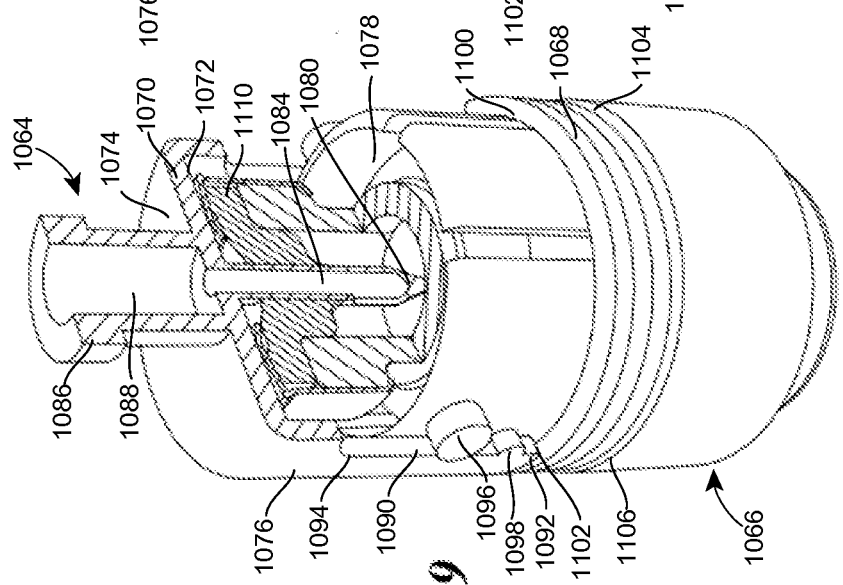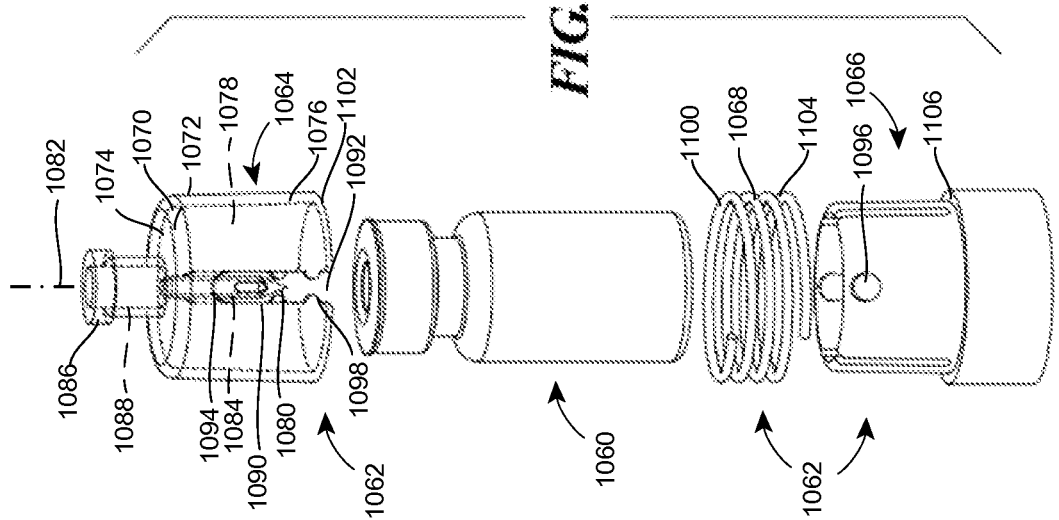

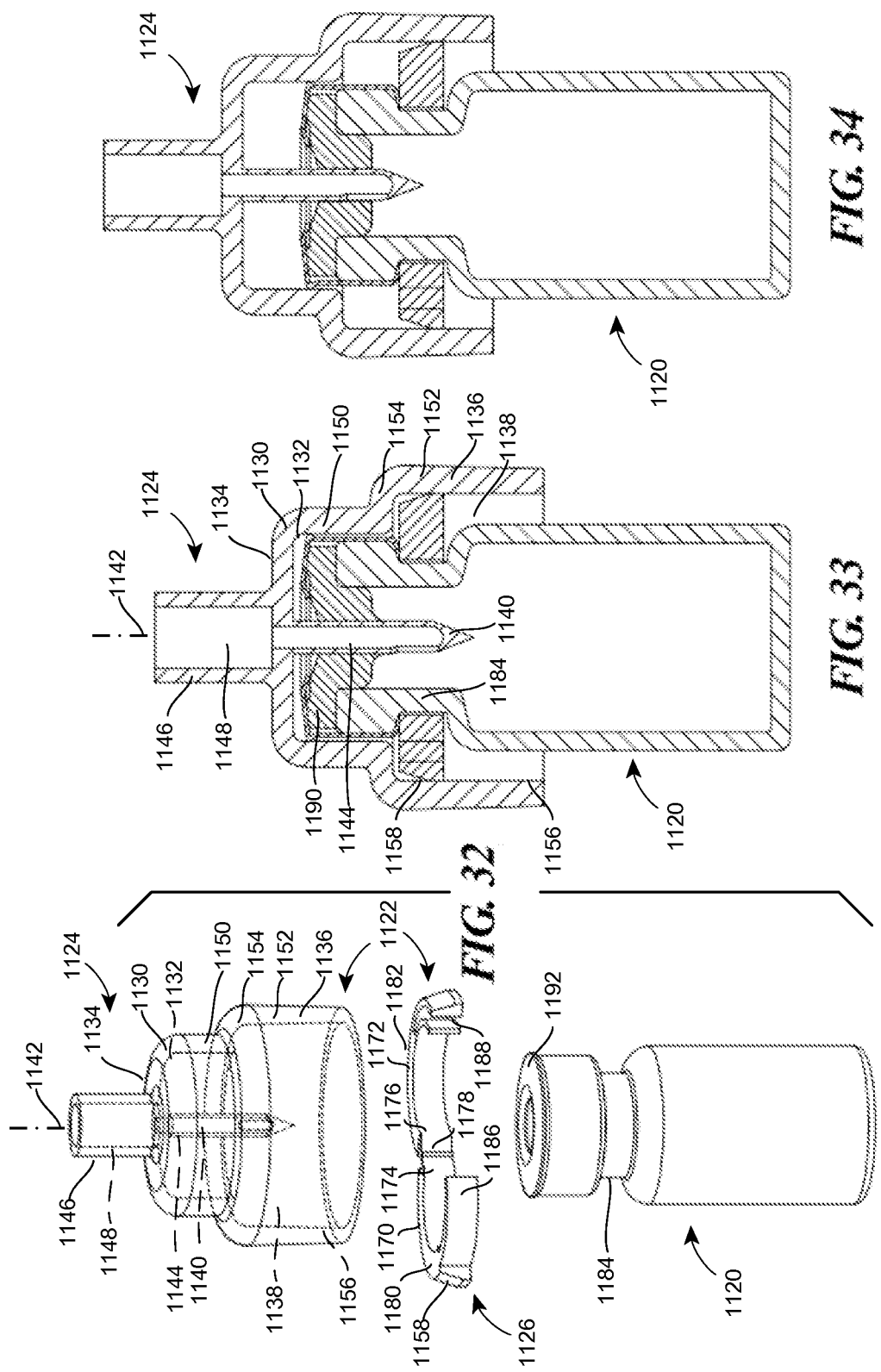

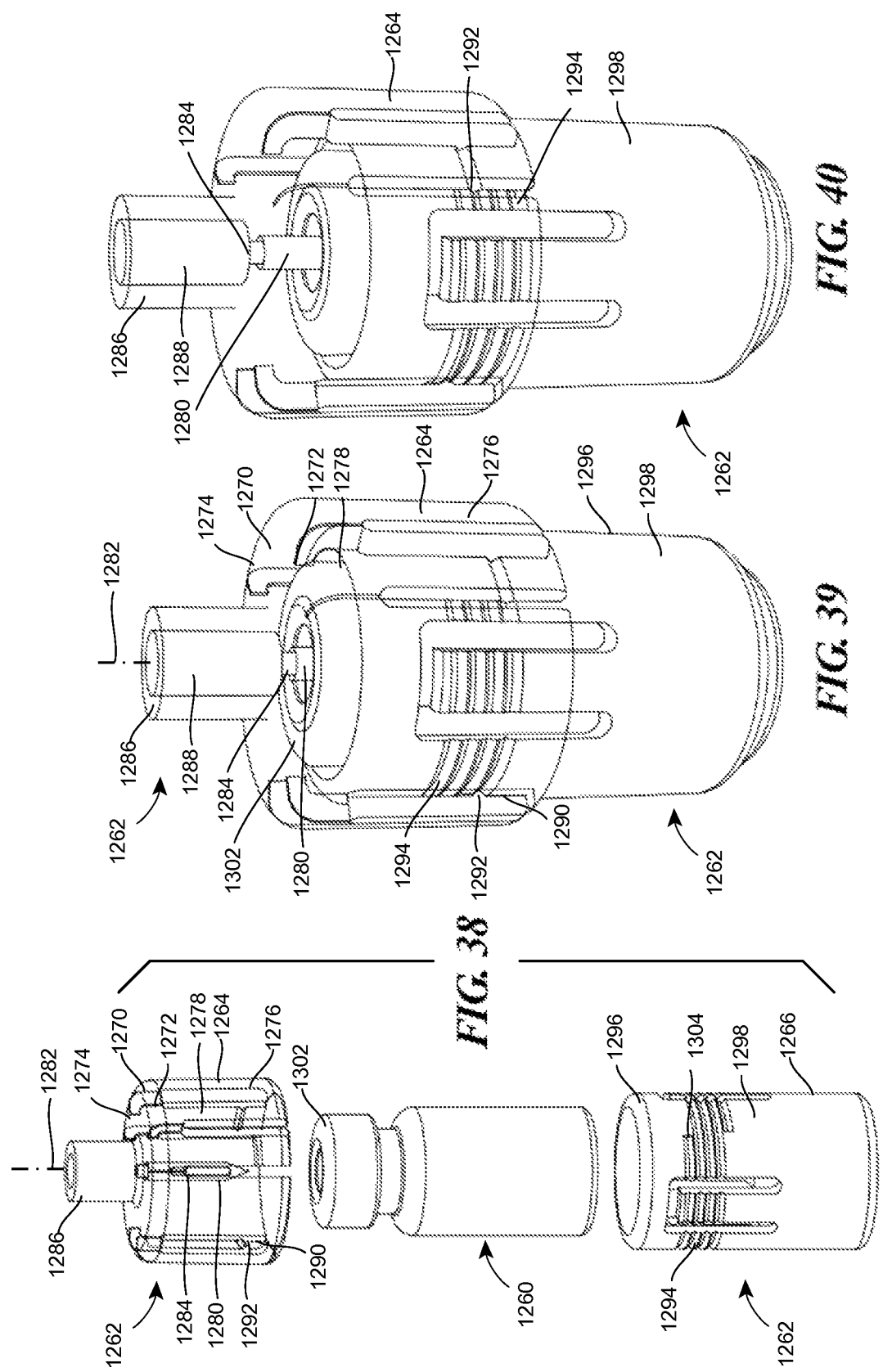

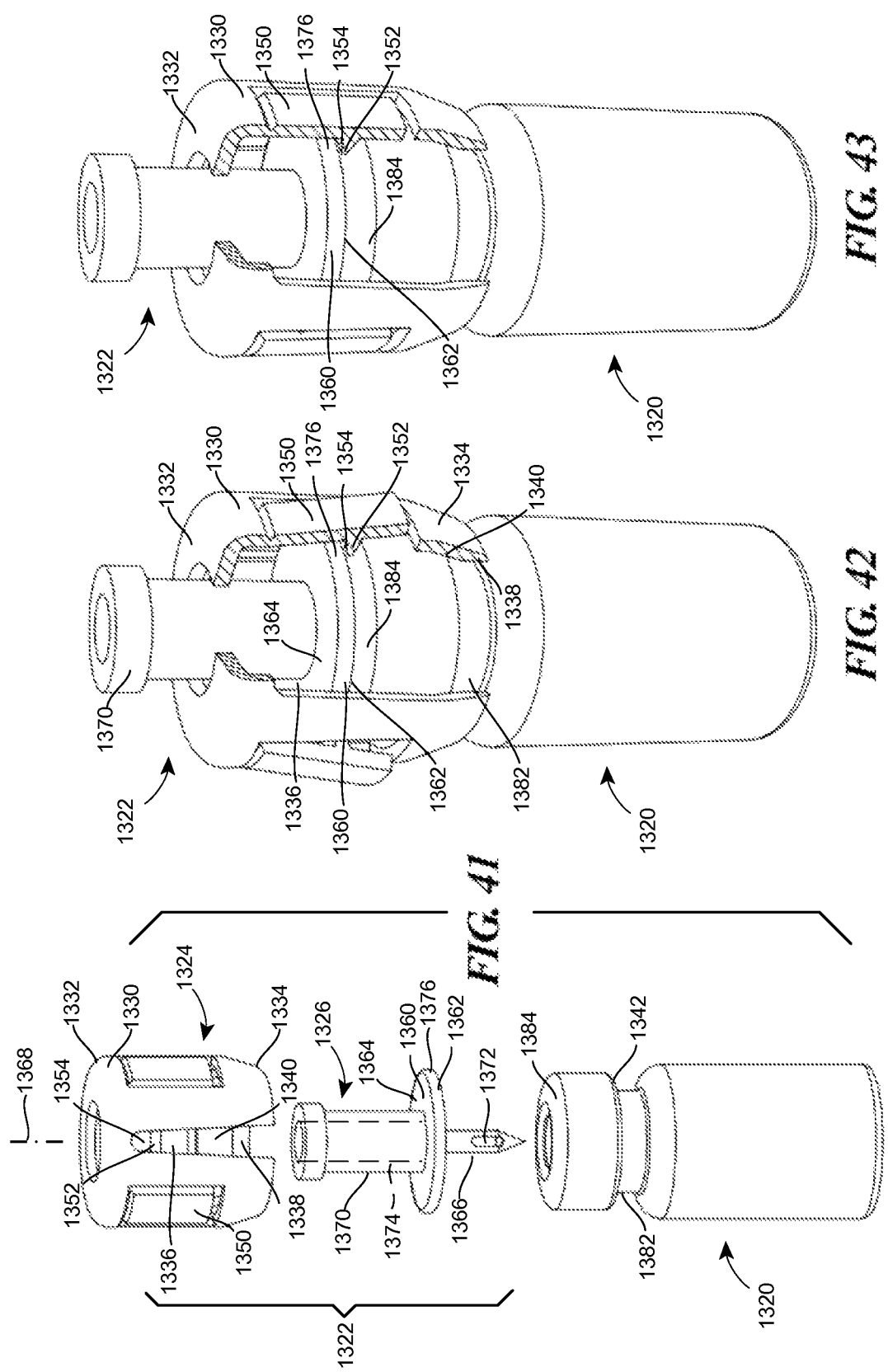

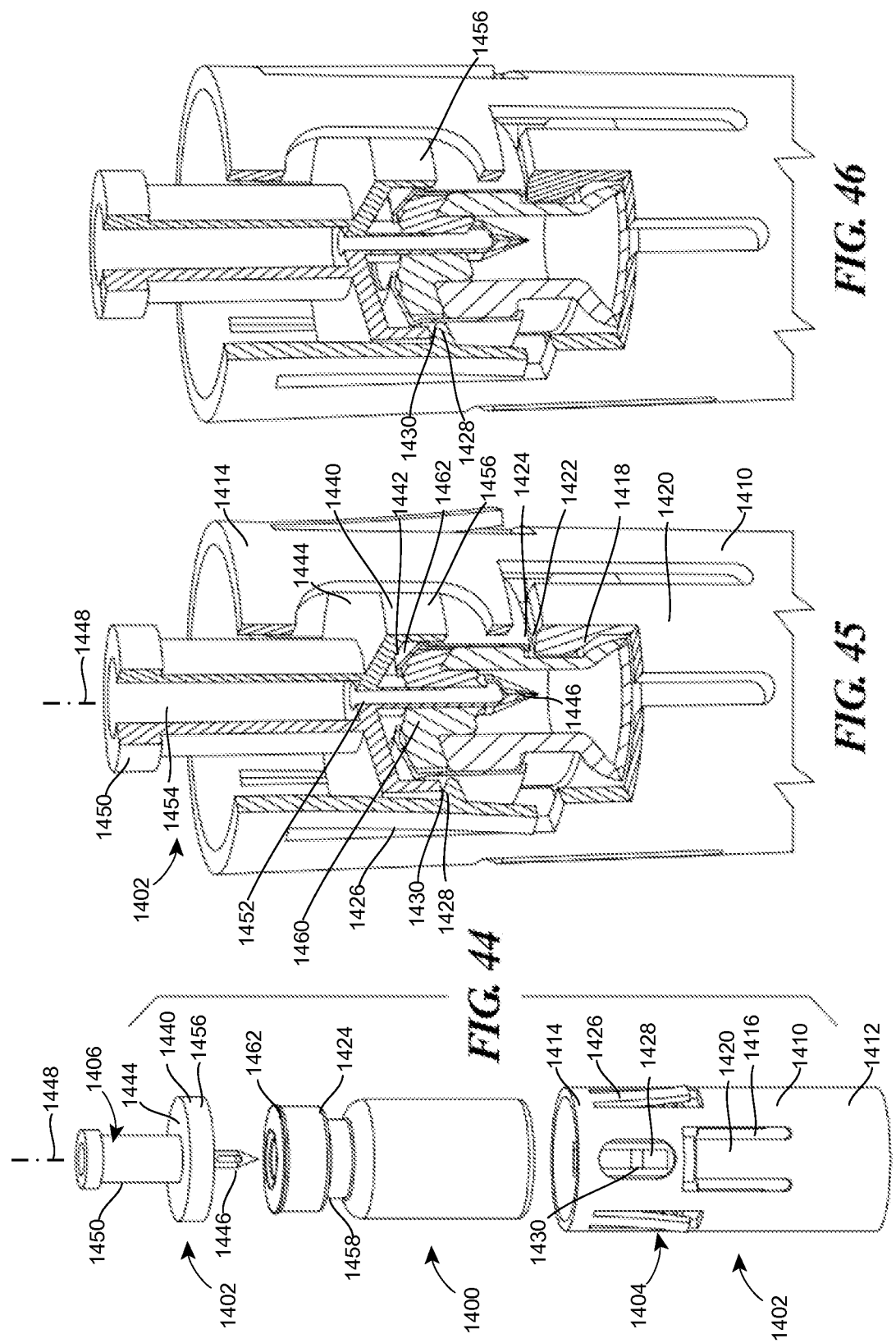

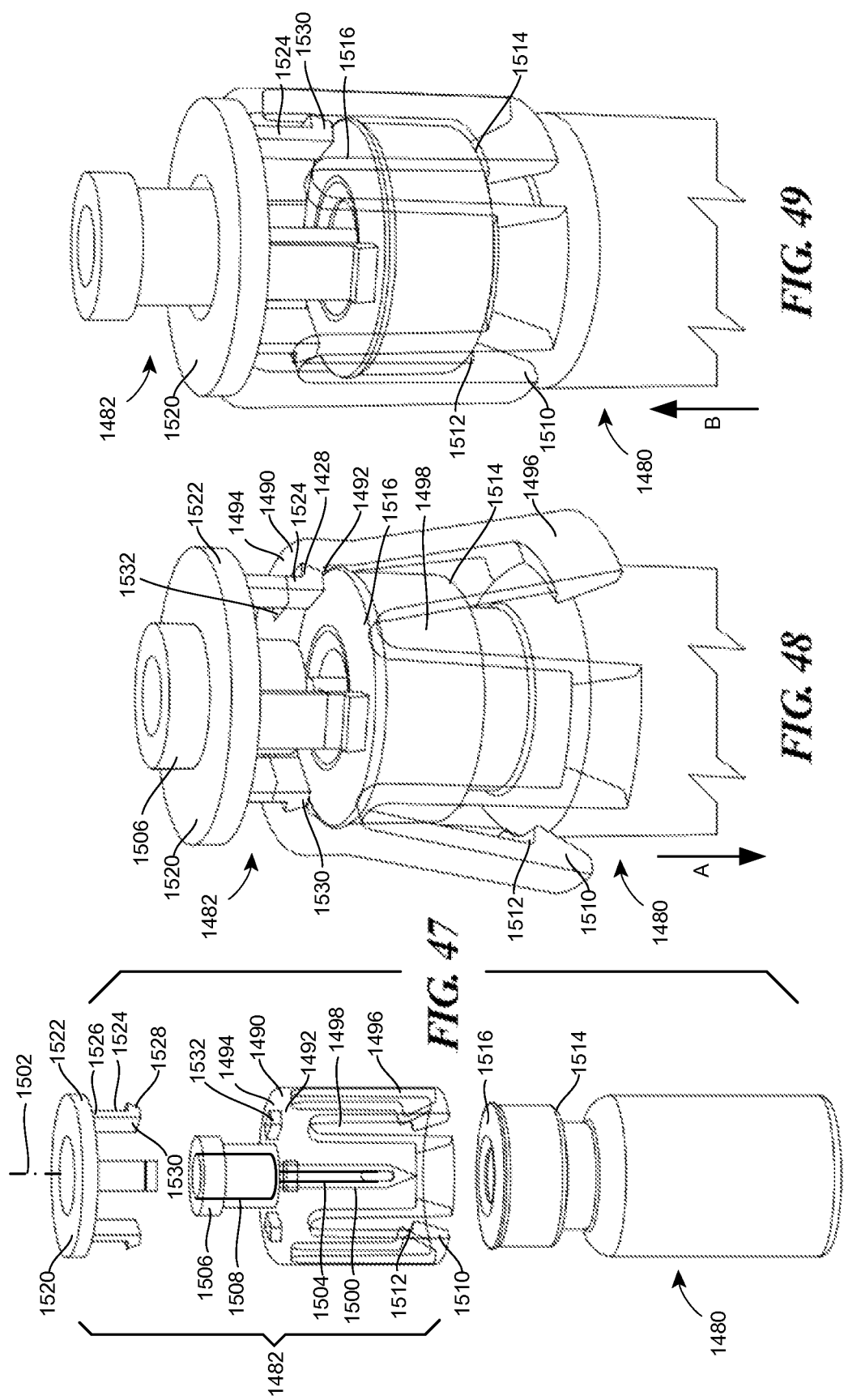

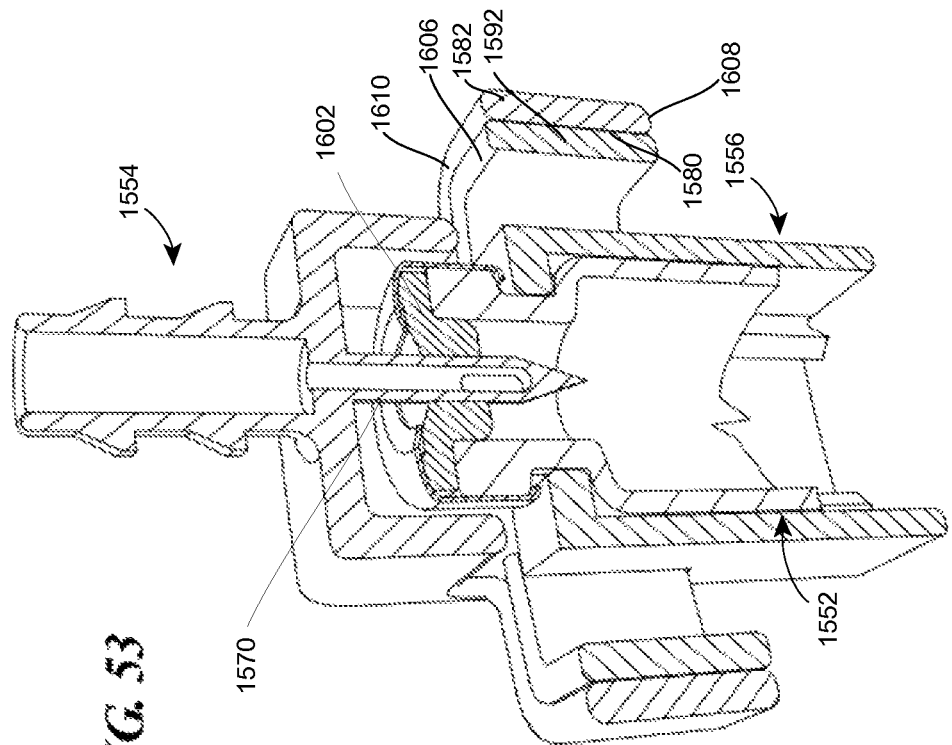
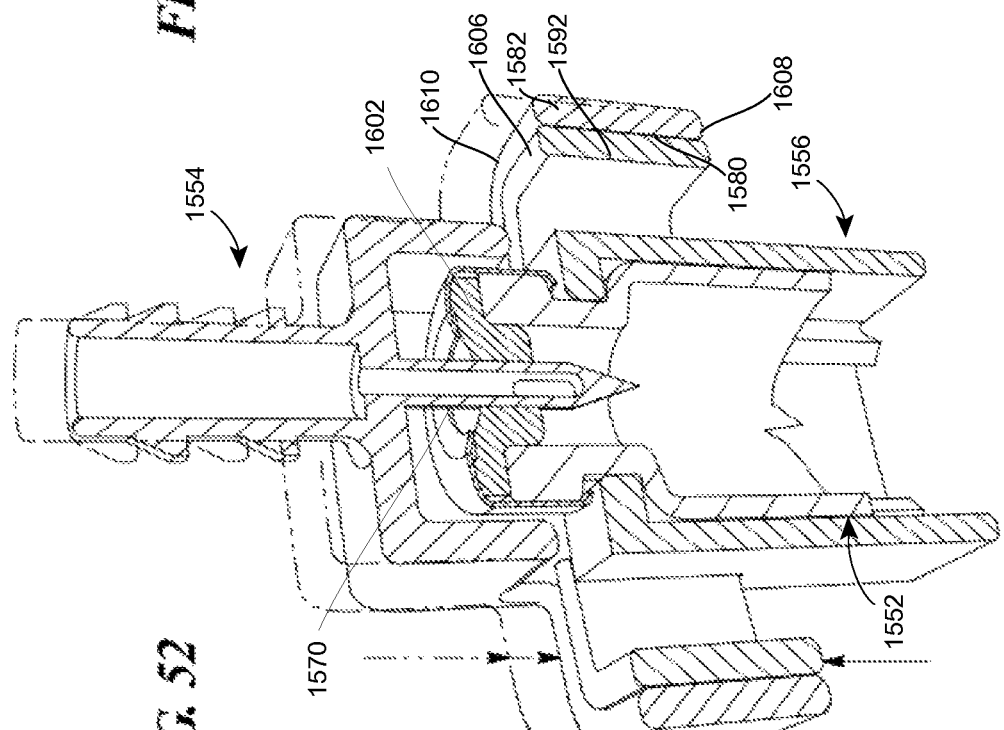

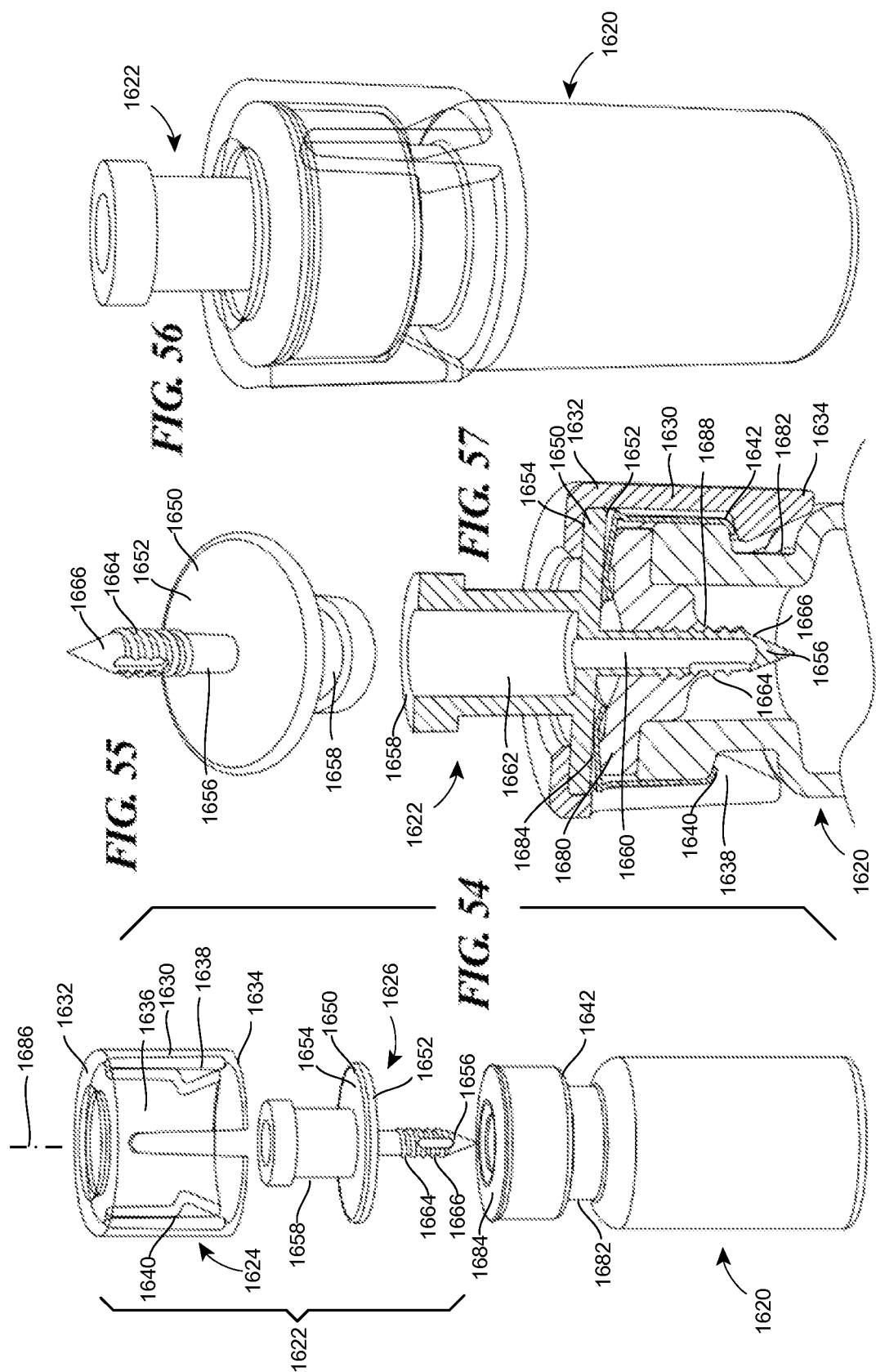

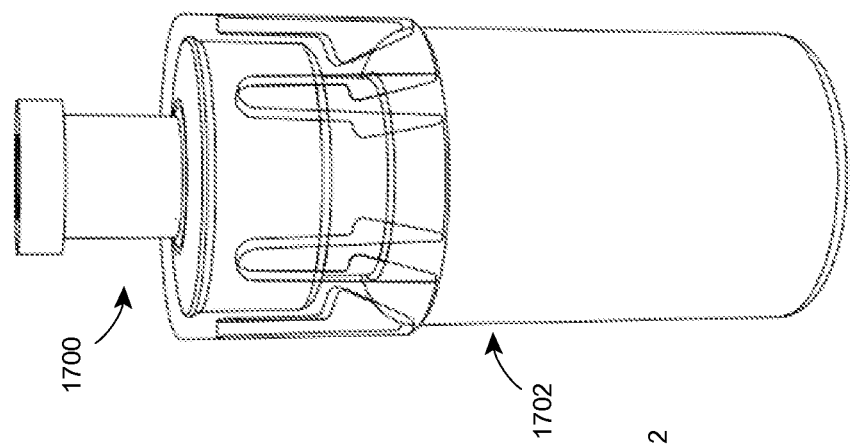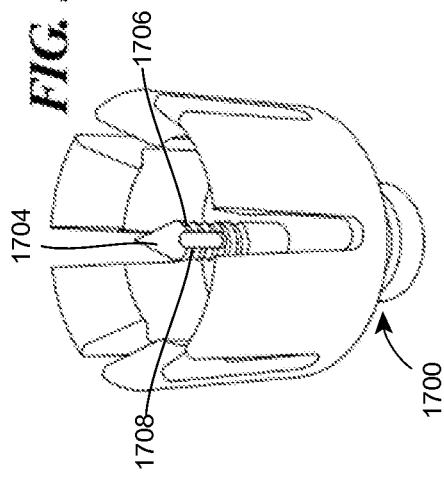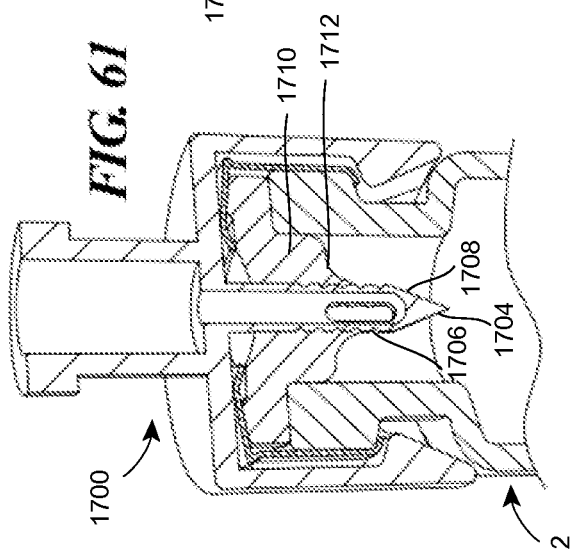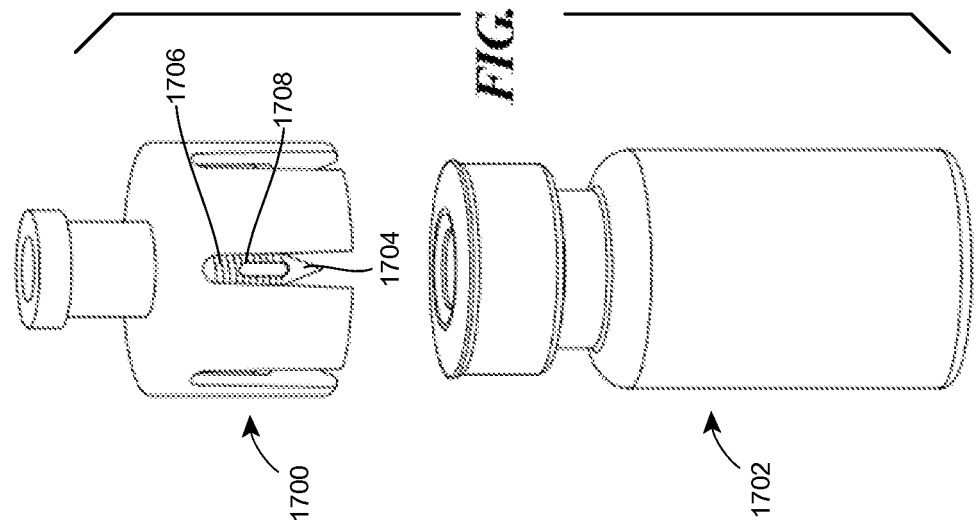

VIAL ADAPTER AND SYSTEM

This is the U.S national phase of International Application No. PCT/US2010/053864, filed Oct. 22, 2010, which claims the benefit of U.S. Patent Application Ser. No. 61/254,520, filed Oct. 23, 2009, the entire disclosures of which are hereby incorporated herein by reference.

BACKGROUND

This patent is directed to a vial adapter, and, in particular, to a vial adapter configured to facilitate connection to a vial. The connection to the vial may be needleless or needle-free.

Pharmaceutical products may be packaged in any of a number of different containers for storage and use. For example, the products may be pre-filled into syringes, or pre-mixed in flexible bags. These products may also be disposed in rigid-walled or semi rigid-walled containers having a stopper or valve held in place on one end by a seal or crimp ring. These containers may be referred to as vials or cartridges, although in this document they will be referred to collectively as vials.

In the past, a needle or pointed instrument was used to advance into the stopper or valve and draw material from the vial. Because a needle or other pointed instrument was involved in drawing material from the container, this procedure had its drawbacks. The use of the needle or other pointed instrument created the potential for accidental sticks of the healthcare workers and/or the patient. The needle also had the potential to puncture equipment, causing damage.

As set forth in more detail below, the present disclosure sets forth an improved adapter embodying advantageous alternatives to the conventional devices and methods discussed above.

SUMMARY

In an aspect of the present disclosure, a system includes a vial having a neck with a passage in the neck and a rim disposed adjacent the neck. The system also includes a stopper disposed over the passage in the neck of the vial to control access through the passage into the vial, and a crimp ring disposed about the stopper and the rim to maintain the stopper fixed relative to the vial. The system further includes a vial adapter including a collar securely attached to the vial at the neck of the vial that receives one of a pair of opposing forces to limit the movement of the stopper relative to the vial.

In another aspect of the present disclosure, a vial adapter includes a base having first and second opposing sides, a tubular skirt depending from the first side of the base, the tubular skirt bounding a space to receive a vial therein, and a spike depending from the first side of the base into the space, the spike having a longitudinal axis and a spike passageway. The tubular skirt has at least one slot formed therein, the at least one slot having a first section that extends parallel to the longitudinal axis of the spike and a second section extending in an arc about the longitudinal axis and connected to the first section. The vial adapter also includes a connector disposed on the second side of the base, the connector having a connector passageway that is in fluid communication with the spike passageway.

In yet another aspect of the present disclosure, a vial adapter includes a base having first and second opposing sides, and a spike depending from the first side of the base, the spike having a longitudinal axis and a spike passageway. The spike has a shaft connected to the base and a head connected to the shaft, the head having a cross-section in a plane orthogonal to the longitudinal axis that is larger in cross-section than the shaft. The vial adapter also includes a biasing mechanism disposed about the spike, and a connector disposed on the second side of the base, the connector having a connector passageway that is in fluid communication with the spike passageway.

In a further aspect of the present disclosure, a system includes a vial adapter and a vial. The vial adapter includes a base having first and second opposing sides, a tubular skirt depending from the first side of the base, the tubular skirt bounding a space, and a spike depending from the first side of the base into the space, the spike having a longitudinal axis and a spike passageway. The tubular skirt has at least one slot formed therein, the at least one slot having a first section that extends parallel to the longitudinal axis of the spike and a second section extending in an arc about the longitudinal axis and connected to the first section. The vial adapter includes a connector disposed on the second side of the base, the connector having a connector passageway that is in fluid communication with the spike passageway. The vial has first and second ends and a receptacle therebetween. The first end of the vial is disposed within the space bounded by the tubular skirt, and has at least one radially-outwardly depending tab that is disposed in the at least one slot, wherein at least one tab is disposed in the second section of the slot in a fully assembled state.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 1 is a perspective view of a vial adapter according to an embodiment of the present disclosure;

FIG. 2 is a plan view of the vial adapter of FIG. 1;

FIG. 20 is an exploded view of a vial adapter configured to address the trapped residual volume of FIG. 19 in combination with a vial;

FIG. 21 is a cross-sectional view of the vial adapter of FIG. 20 in a first position relative to the vial;

FIG. 22 is a cross-sectional view of the vial adapter of FIG. 20 in a second position relative to the vial;

FIG. 23 is an exploded view of an alternative vial adapter configured to address the trapped residual volume of FIG. 19 in combination with a vial;

FIG. 24 is a cross-sectional view of the vial adapter of FIG. 23 in a first position relative to the vial;

FIG. 25 is a cross-sectional view of the vial adapter of FIG. 23 in a second position relative to the vial;

FIG. 26 is an exploded view of a second alternative vial adapter configured to address the trapped residual volume of FIG. 19 in combination with a vial;

FIG. 27 is a cross-sectional view of the vial adapter of FIG. 26 in a first position relative to the vial;

FIG. 28 is a cross-sectional view of the vial adapter of FIG. 26 in a second position relative to the vial;

FIG. 29 is an exploded view of a third alternative vial adapter configured to address the trapped residual volume of FIG. 19 in combination with a vial;

FIG. 30 is a partial cross-sectional view of the vial adapter of FIG. 29 in a first position relative to the vial;

FIG. 31 is a partial cross-sectional view of the vial adapter of FIG. 29 in a second position relative to the vial;

FIG. 32 is an exploded view of a fourth alternative vial adapter configured to address the trapped residual volume of FIG. 19 in combination with a vial;

FIG. 33 is a cross-sectional view of the vial adapter of FIG. 32 in a first position relative to the vial;

FIG. 34 is a cross-sectional view of the vial adapter of FIG. 32 in a second position relative to the vial;

FIG. 38 is an exploded view of a sixth alternative vial adapter configured to address the trapped residual volume of FIG. 19 in combination with a vial;

FIG. 39 is a perspective view of the vial adapter of FIG. 38 in a first position relative to the vial;

FIG. 40 is a perspective view of the vial adapter of FIG. 38 in a second position relative to the vial;

FIG. 41 is an exploded view of a seventh alternative vial adapter configured to address the trapped residual volume of FIG. 19 in combination with a vial;

FIG. 42 is a partial cross-sectional view of the vial adapter of FIG. 41 in a first position relative to the vial;

FIG. 43 is a partial cross-sectional view of the vial adapter of FIG. 41 in a second position relative to the vial;

FIG. 44 is an exploded view of an eighth alternative vial adapter configured to address the trapped residual volume of FIG. 19 in combination with a vial;

FIG. 45 is a partial cross-sectional view of the vial adapter of FIG. 44 in a first position relative to the vial;

FIG. 46 is a partial cross-sectional view of the vial adapter of FIG. 44 in a second position relative to the vial;

FIG. 47 is an exploded view of a ninth alternative vial adapter configured to address the trapped residual volume of FIG. 19 in combination with a vial;

FIG. 48 is a perspective view of the vial adapter of FIG. 47 in a first position relative to the vial;

FIG. 49 is a perspective view of the vial adapter of FIG. 47 in a second position relative to the vial;

FIG. 52 is a cross-sectional view of the vial adapter of FIG. 50 in a second position relative to the vial;

FIG. 53 is a cross-sectional view of the vial adapter of FIG. 50 in a second position relative to the vial;

FIG. 54 is an exploded view of an eleventh vial adapter configured to address the trapped residual volume of FIG. 19 in combination with a vial;

FIG. 55 is an enlarged perspective view of the spike subassembly according to the vial adapter of FIG. 54;

FIG. 56 is a perspective view of the vial adapter of FIG. 54 with the spike subassembly being rotated about its central axis;

FIG. 57 is an enlarged cross-sectional view of the vial adapter of FIG. 54 as the spike subassembly is rotated about its central axis, illustrating the movement of the stopper surface in phantom;

FIG. 58 is an exploded view of a twelfth vial adapter configured to address the trapped residual volume of FIG. 19 in combination with a vial;

FIG. 59 is an enlarged perspective view of the spike subassembly according to the vial adapter of FIG. 58;

FIG. 60 is a perspective view of the vial adapter of FIG. 58 with the spike subassembly being rotated about its central axis;

FIG. 61 is an enlarged cross-sectional view of the vial adapter of FIG. 58 as the spike subassembly is rotated about its central axis, illustrating the movement of the stopper surface in phantom;

DETAILED DESCRIPTION OF VARIOUS EMBODIMENTS

Although the following text sets forth a detailed description of different embodiments of the invention, it should be understood that the legal scope of the invention is defined by the words of the claims set forth at the end of this patent. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent, which would still fall within the scope of the claims defining the invention.

Figure 10:
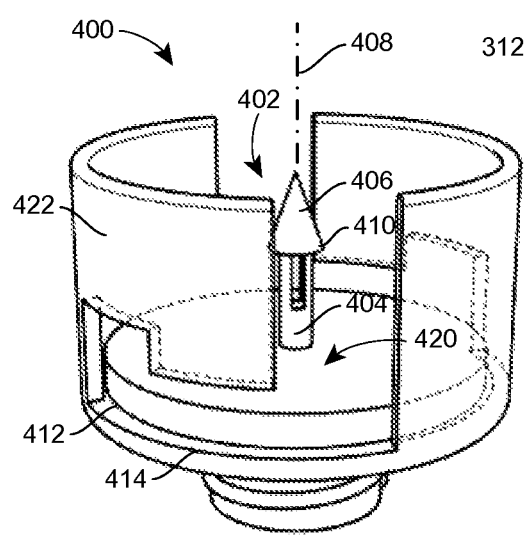
FIG. 10 is a perspective view of a vial adapter according to a third alternative embodiment.

Along these lines, FIGS. 1 and 2 illustrate an embodiment of a vial adapter 100. The vial adapter 100 may be used with a vial 102, such as is illustrated in FIGS. 3-6, and may be packaged with the vial 102 as a kit. While a particular adapter 100 is illustrated in FIGS. 1 and 2, and in combination with a particular vial 102 in FIGS. 3-6, it will be recognized that numerous variants are possible as to the adapter and the vial, certain of which are illustrated herein and others of which would occur to one skilled in the art with reference to the illustrations herein. For example, certain features illustrated in the embodiment of the adapter of FIGS. 1 and 2 and other features illustrated in the embodiment of FIG. 10 may be combined in an embodiment not illustrated, but within the scope of the present disclosure (e.g., a vial adapter as illustrated in FIGS. 1 and 2 with a spike as illustrated in the embodiment of FIG. 10).

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

Discussing the vial adapter 100 and vial 102 first in general terms with reference to FIGS. 1-6, it will be recognized that the vial adapter 100 includes a base 110 having first and second opposing sides 112, 114 (see FIGS. 1 and 2). A tubular skirt 116 may depend from the first side 112 of the base 110, the tubular skirt 116 bounding a space 118 to receive a vial, such as the vial 102, therein. A spike 120 may depend from the first side 112 of the base 110 into the space 118. The spike 120 may have a longitudinal axis 122 (see FIG. 1) and a spike passageway 124 (see FIGS. 2 and 3). The vial adapter 100 may also include a connector 126 disposed on the second side 114 of the base 110, the connector 114 having a connector passageway 128 that is in fluid communication with the spike passageway 124 (see FIGS. 2 and 3). The base 110, skirt 116, spike 120 and connector 126 may be formed (e.g., molded) as a single unit out of polycarbonate, for example. The connector 126 may be a luer lock connection for connecting with a syringe or tubing, or alternatively may be smooth for connecting to tubing.

As is also illustrated in FIGS. 1 and 2, the tubular skirt 116 may have at least one slot 130 formed therein. As will be illustrated in later embodiments, the skirt 116 may have no slots; in still other embodiments, the skirt may be absent entirely. According to the embodiment illustrated in FIGS. 1 and 2, the at least one slot 130 may have a first section 132 that extends parallel to the longitudinal axis 122 of the spike 120, and a second section 134 extending in an arc about the longitudinal axis 122 and connected to the first section 132.

As mentioned above, the vial adapter 100 may be used with a vial 102. The vial 102 may contain a pharmaceutical product, such as an erythropoiesis stimulating agent (ESA), which may be in a liquid or a lyophilized form. An ESA is any molecule that stimulates erythropoiesis, such as Epogen® (Epoetin alfa), Aranesp® (Darbepoetin alfa), Dynepo (Epoetin delta), Mircera (methyoxy polyethylene glycol-epoetin beta), Hematide, MRK-2578, INS-22, Retacrit (Epoetin zeta), Neorecormon (Epoetin beta), Silapo (Epoetin zeta), Binocrit (Epoetin alfa), Epoetin alfa Hexal, Abseamed (Epoetin alfa), Ratioepo (Epoetin theta), Eporatio (Epoetin theta), Biopoin (Epoetin theta), Epoetin alfa, Epoetin beta, Epoetin Zeta, Epoetin Theta, and Epoetin delta, as well as the molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publ. Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publ. Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; US Publ. Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/

0111279; and PCT Publ. Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Alternatively, the vial 102 may contain other products. Examples of other pharmaceutical products that may be contained in the vial 102 may include, but are not limited to, therapeutics such as a biological (e.g., Enbrel® (etanercept, TNF-receptor/Fc fusion protein, TNF blocker), Neulasta® (Pegylated filgastrim, pegylated G-CSF, pegylated hu-Met-G-CSF), Neupogen® (Filgrastim, G-CSF, hu-MetG-CSF), Nplate® (Romiplostim), Vectibix® (Panitumumab), Sensipar® (Cinacalcet), and Denosamab® (AMG 162)), a small molecule drug, a therapeutic antibody, a polypeptide, a protein or other chemical, such as an iron, for example, ferumoxytol, iron dextrans, ferric glyconate, and iron sucrose. The therapeutic may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publ. No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO: 2 as set forth therein in FIG. 2 and/or the heavy chain of SEQ ID NO:4, as set forth therein in FIG. 4, each of which is individually and specifically incorporated by reference herein in its entirety fully as disclosed in the foregoing Publication;

Myostatin binding proteins, peptibodies, and related proteins, and the like, including myostatin specific peptibodies, particularly those described in US Publ. No. 2004/0181033 and PCT Publ. No. WO 2004/058988, which are incorporated by reference herein in their entirety particularly in parts pertinent to myostatin specific peptibodies, including but not limited to peptibodies of the mTN8-19 family, including those of SEQ ID NOS: 305-351, including TN8-19-1 through TN8-19-40, TN8-19 con1 and TN8-19 con2; peptibodies of the mL2 family of SEQ ID NOS: 357-383; the mL15 family of SEQ ID NOS: 384-409; the mL17 family of SEQ ID NOS: 410-438; the mL20 family of SEQ ID NOS: 439-446; the mL21 family of SEQ ID NOS: 447-452; the mL24 family of SEQ ID NOS: 453-454; and those of SEQ ID NOS: 615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publ. No. WO 2005/047331 or PCT Appl. No. PCT/US2004/03742 and in US Publ. No. 2005/112694, which are incorporated herein by reference in there entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publ. No. 2004/097712A1, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned U.S. publication;

Ang2 specific antibodies, peptibodies, and related proteins, and the like, including but not limited to those described in PCT Publ. No. WO 03/057134 and U.S. Publ No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publ. No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1K, Ab1P; and Ab1P, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in US Publ. No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publ. No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50HS0, L51H51, L52H52, and IGF-1R-binding fragments and derivatives thereof, each of which is individually and specifically incorporated by reference herein in its entirety fully as disclosed in the foregoing International Publication;

Also among non-limiting examples of anti-IGF-1R antibodies for use in the methods and compositions of the present invention are each and all of those described in:

(i) US Publ. No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publ. No. WO 06/138729 (published Dec. 28, 2006) and WO 05/016970 (published Feb. 24, 2005), and Lu et al., 2004, J. Biol. Chem. 279:2856-65, including but not limited to antibodies 2F8, A12, and IMC-A12 as described therein;

(iii) PCT Publ. No. WO 07/012,614 (published Feb. 1, 2007), WO 07/000,328 (published Jan. 4, 2007), WO 06/013472 (published Feb. 9, 2006), WO 05/058967 (published Jun. 30, 2005), and WO 03/059951 (published Jul. 24, 2003);

(iv) US Publ. No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) US Publ. Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al., 2003, Cancer Res. 63:5073-83, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), US Publ. Nos. 2005/0244408 (published Nov. 30, 2005) and 2004/0086503 (published May 6, 2004), and Cohen, et al., 2005, Clinical Cancer Res. 11:2063-73, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) US Publ. Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) US Publ. No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publ. No. 2008/0166352 and PCT Publ. No. WO 07/011,941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing U.S. Publication;

IL-15 specific antibodies, peptibodies, and related proteins, and the like, such as, in particular, humanized monoclonal antibodies, particularly antibodies such as those disclosed in U.S. Publ. Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in US Publ. No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing US Publication and in Thakur et al., Mol. Immunol. 36:1107-1115 (1999). In addition, description of the properties of these antibodies provided in the foregoing US publication is also incorporated by reference herein in its entirety. Specific antibodies include those having the heavy chain of SEQ ID NO: 17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing US Publication. A specific antibody contemplated is antibody 1119 as disclosed in foregoing US Publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publ. Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing US Publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in US Publ. No. 2005/0118643 and PCT Publ. No. WO 2005/017107, huL2G7 described in U.S. Pat. No. 7,220,410 and OA-5d5 described in U.S. Pat. Nos. 5,686,292 and 6,468,529 and in PCT Publ. No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in US Publ. No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and US Publ. No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publ. No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO: 8 and a light chain variable region having SEQ ID NO: 6 as disclosed in the International Publication;

c-Kit specific antibodies, peptibodies, related proteins, and the like, including but not limited to those described in Publ. No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. application Ser. No. 11/068,289, which is incorporated herein by reference in its entirety, particularly in parts pertinent to proteins that bind OX40L and/or other ligands of the OXO40 receptor; and Other exemplary proteins, including Activase® (Alteplase, tPA); Aranesp® (Darbepoetin alfa), Epogen® (Epoetin alfa, or erythropoietin); Avonex® (Interferon beta-1a); Bexxar® (Tositumomab, anti-CD22 monoclonal antibody); Betaseron® (Interferon-beta); Campath® (Alemtuzumab, anti-CD52 monoclonal antibody); Dynepo® (Epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (Epoetin alfa); Erbitux® (Cetuximab, anti-EGFR/HER1/c-ErbB-1); Genotropin® (Somatropin, Human Growth Hormone); Herceptin® (Trastuzumab, anti-HER2/neu (erbB2) receptor mAb); Humatrope® (Somatropin, Human Growth Hormone); Humira® (Adalimumab); Insulin in Solution; Infergen® (Interferon Alfacon-1); Natrecor® (nesiritide; recombinant human B-type natriuretic peptide (hBNP); Kineret® (Anakinra), Leukine® (Sargamostim, rhuGM-CSF); LymphoCide® (Epratuzumab, anti-CD22 mAb); Lymphostat B® (Belimumab, anti-BlyS mAb); Metalyse® (Tenecteplase, t-PA analog); Mircera® (methoxy polyethylene glycol-epoetin beta); Mylotarg® (Gemtuzumab ozogamicin); Raptiva® (efalizumab); Cimzia® (certolizumab pegol, CDP 870); Soliris™ (Eculizumab); Pexelizumab (Anti-05 Complement); MEDI-524 (Numax®); Lucentis® (Ranibizumab); 17-1A (Edrecolomab, Panorex®); Trabio® (lerdelimumab); TheraCim hR3 (Nimotuzumab); Omnitarg (Pertuzumab, 2C4); Osidem® (IDM-1); OvaRex® (B43.13); Nuvion® (visilizumab); Cantuzumab mertansine (huC242-DM1); NeoRecormon® (Epoetin beta); Neumega® (Oprelvekin, Human Interleukin-11); Neulasta® (Pegylated filgastrim, pegylated G-CSF, pegylated hu-Met-G-CSF); Neupogen® (Filgrastim, G-CSF, hu-MetG-CSF); Orthoclone OKT3® (Muromonab-CD3, anti-CD3 monoclonal antibody), Procrit® (Epoetin alfa); Remicade® (Infliximab, anti-TNFα monoclonal antibody), Reopro® (Abciximab, anti-GP IIb/IIia receptor monoclonal antibody), Actemra® (anti-IL6 Receptor mAb), Avastin® (Bevacizumab), HuMax-CD4 (zanolimumab), Rituxan® (Rituximab, anti-CD20 mAb); Tarceva® (Erlotinib); Roferon-A®-(Interferon alfa-2a); Simulect® (Basiliximab); Prexige® (lumiracoxib); Synagis® (Palivizumab); 146B7-CHO (anti-IL15 antibody, see U.S. Pat. No. 7,153,507), Tysabri® (Natalizumab, anti-α4integrin mAb); Valortim® (MDX-1303, anti-B. anthracis Protective Antigen mAb); ABthrax™; Vectibix® (Panitumumab); Xolair® (Omalizumab), ETI211 (anti-MRSA mAb), IL-1 Trap (the Fc portion of human IgG1 and the extracellular domains of both IL-1 receptor components (the Type I receptor and receptor accessory protein)), VEGF Trap (Ig domains of VEGFR1 fused to IgG1 Fc), Zenapax® (Daclizumab); Zenapax® (Daclizumab, anti-IL-2Rα mAb), Zevalin® (Ibritumomab tiuxetan), Zetia (ezetimibe), Atacicept (TACI-Ig), anti-CD80 monoclonal antibody (mAb) (galiximab), anti-CD23 mAb (lumiliximab), BR2-Fc (huBR3/huFc fusion protein, soluble BAFF antagonist); CNTO 148 (Golimumab, anti-TNFα mAb); HGS-ETR1 (Mapatumumab; human anti-TRAIL Receptor-1 mAb); HuMax-CD20 (Ocrelizumab, anti-CD20 human mAb); HuMax-EGFR (zalutumumab); M200 (Volociximab, anti-α5β1 integrin mAb); MDX-010 (Ipilimumab, anti-CTLA-4 mAb and VEGFR-1 (IMC-18F1); anti-BR3 mAb; anti-C. difficile Toxin A and Toxin B C mAbs MDX-066 (CDA-1) and MDX-1388); anti-CD22 dsFv-PE38 conjugates (CAT-3888 and CAT-8015); anti-CD25 mAb (HuMax-TAC); anti-CD3 mAb (NI-0401); Adecatumumab; anti-CD30 mAb (MDX-060); MDX-1333 (anti-IFNAR); anti-CD38 mAb (HuMax CD38); anti-CD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; anti-ganglioside GD2 mAb; anti-ganglioside GM2 mAb; anti-GDF-8 human mAb (MYO-029); anti-GM-CSF Receptor mAb (CAM-3001); anti-HepC mAb (HuMax HepC); anti-IFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1 mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Figure 3:
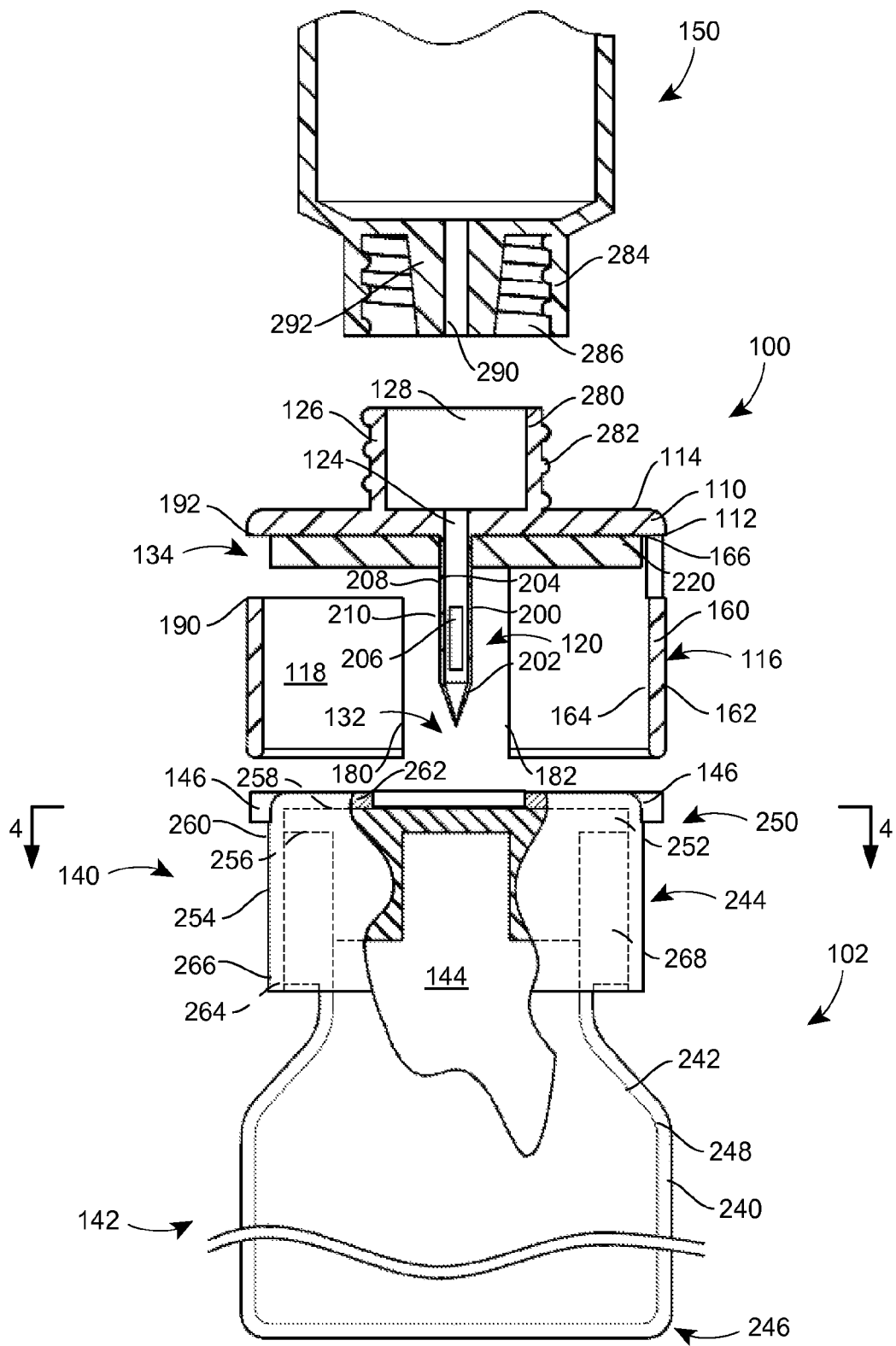
FIG. 3 is a cross-sectional view of the vial adapter of FIG. 1 taken about line 3-3 in FIG. 2, in combination with a syringe also shown in cross-section and a vial shown in partial cross-section.
Figure 5:
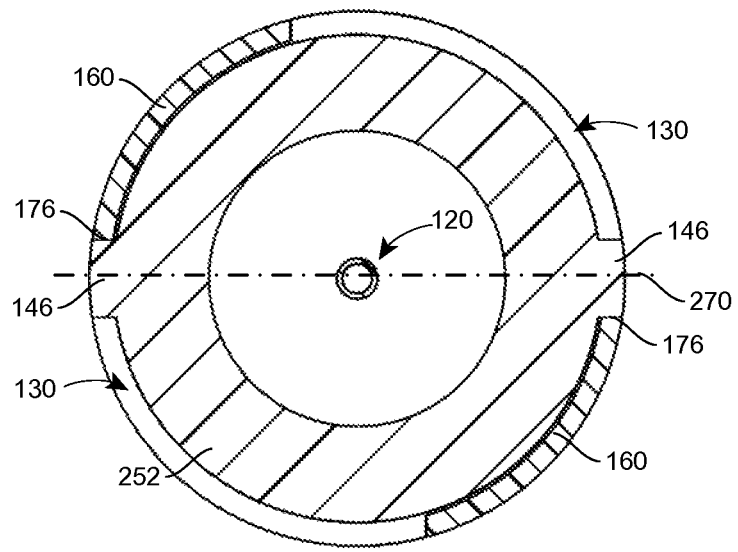
FIG. 5 is a cross-sectional view of the combination of the vial adapter and the vial in a second (or locked) orientation (or state) relative to each other.
Figure 6:
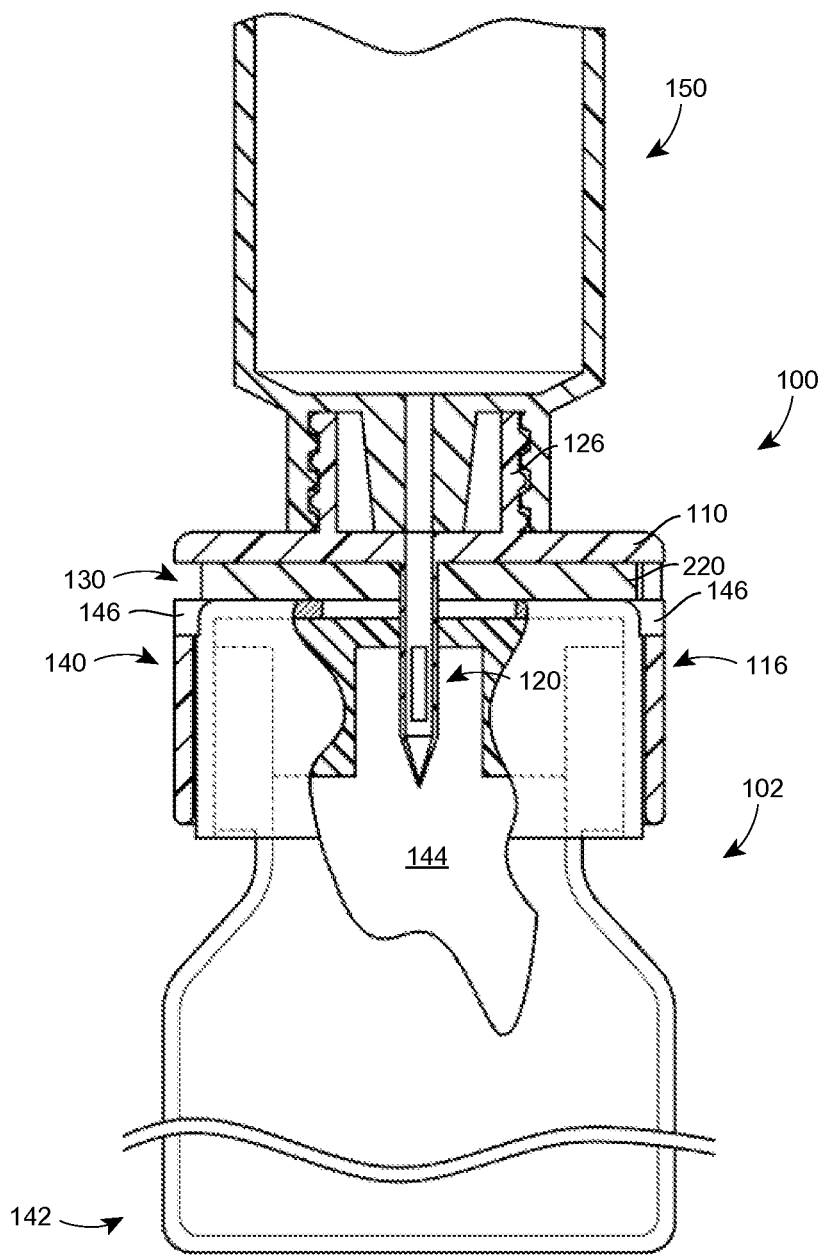
FIG. 6 is a cross-sectional view of the combination of the vial adapter, vial and syringe of FIG. 3 as assembled.

As illustrated in FIGS. 3 and 6, the vial 102 may have first and second ends 140, 142 and a receptacle 144 therebetween. The first end 140 of the vial 102 may be disposed with the space 118 bounded by the tubular skirt 116. The vial 102 may have at least one radially-outwardly depending tab 146 at the first end of the vial 102, the tab 146 being disposed in the at least one slot 130. In particular, the at least one tab 146 may be disposed in the second section 134 of the slot 130 in a fully assembled state, as illustrated in FIGS. 5 and 6.

With the vial adapter 100 and the vial 102 so assembled, the vial adapter 100 may be connected, via the connector 126 to any of a number of different devices or systems. For example, a device 150 in the form of a syringe has been illustrated in FIGS. 3 and 6, while a device 152 in the form of a machine has been illustrated in FIG. 7. In fact, it will be recognized the connector 126 may be used to connect the vial adapter 100 and associated vial 102 to an administration set including needleless or needle-free connectors, or even directly to tubing without the use of needless or needle-free connectors. The structure of the connector 126 may vary according to the device or system that is sought to be connected to the adapter 100 and vial 102. In various embodiments, the needleless or needle-free adapter 100 may be held in place on the device or system by appropriate attachments and the vial 102 may then be inserted into the needleless or needle-free adapter 100.

In an embodiment illustrated in FIGS. 3 and 6, the vial adapter 100 may be used according to the following procedure with the vial 102 and the syringe 150 to reconstitute a product contained in the vial 102 and administer the reconstituted product to a patient, for example.

Figure 4:
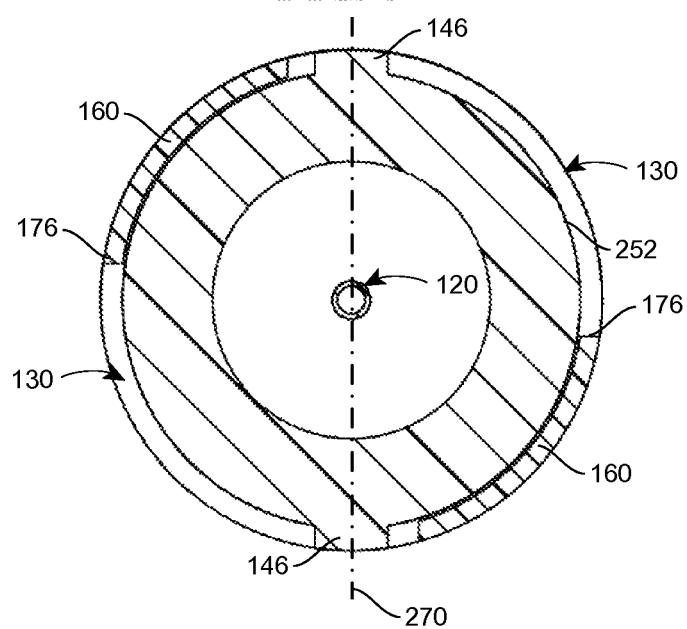
FIG. 4 is a cross-sectional view of the combination of the vial adapter and the vial of FIG. 3 taken about line 4-4 in FIG. 3, with the vial adapter and the vial in a first (or unlocked) orientation (or state) relative to each other.

Holding the vial 102 in one hand, the vial adapter 100 is held in the other hand with the spike 120 oriented in the direction of the vial 102, as illustrated in FIG. 3. The adapter 100 or the vial 102 is rotated to align the tabs 146 with the first sections 132 of the slots 130, such as illustrated in FIG. 4. The adapter 100 may then be advanced in the direction of the vial 102, the tabs 146 cooperating with the first sections 132 of the slots 130 to guide the motion of the adapter 100 so that it is primarily along the axis 122 of the spike 120. Therefore, the spike 120 will be advanced into the vial 102 so that the spike passage 124 is in fluid communication with the receptacle 144 of the vial 102.

To secure the adapter 100 to the vial 102, the adapter 100 is rotated or twisted about the axis 122. According to one embodiment of the present procedure, the adapter 100 is rotated or twisted until the tabs 146 traverse the entire length of the second sections 134 of the slots 130, such that the tabs 146 move along the section sections 134 between the state illustrated in FIG. 4 and the state illustrated in FIG. 5. The state illustrated in FIG. 4 may be referred to as the unlocked state, while the state in FIG. 5 may be referred to as the locked state.

With the adapter 100 secured to the vial 102, the syringe 150 may be attached to the connector 126. As illustrated, the syringe 150 may be rotated relative to the adapter 100 to engage threads on the connector 126 with threads on the syringe 150. The threaded engagement between the syringe 150 and the adapter 100 secures the syringe 150 to the adapter, and consequently to the vial 102 which is secured to the adapter 100.

To reconstitute the lyophilized product contained in the vial 102, the syringe 150 may be filled with a suitable diluent. With the syringe 150 secured to the adapter 100, the diluent may be expelled from the syringe 150 through the passage 124 of the spike 120 and into the receptacle 144 of the vial 102. The user may shake or swirl the vial 102 to encourage the interaction between the diluent and the product in the vial 102, thereby encouraging the reconstitution of the product.

According to one embodiment, the syringe 150 may also be used to draw the reconstituted product from the vial 102, whereupon the syringe 150 may be used to administer the product to a patient intravenously using a needle or by connecting the syringe 150 to a needleless or needle-free connector attached to a catheter already introduced into a vein. Alternatively, the vial 102 containing the reconstituted product may be connected to the patient by attaching the connector 126 to a needleless or needle-free connector that is part of an administration set already connected to the patient. In fact, the product may be administered intravenously, subcutaneously, or by any other route deemed appropriate by a medical professional.

As will be recognized, the use of the adapter 100 in a procedure to reconstitute of a product contained in the vial 102 and administer the reconstituted product to a patient is but one possible use for the adapter 100. Instead, the adapter 100 may be used to provide a simple, needleless or needle-free connection between a vial 102 containing a liquid form of a product and a syringe 150. Other uses are also possible. For example, the adapter 100 may be connected via a line to a delivery device in communication with the patient, and then the vial 102 may be secured to the adapter 100 so that the contents may be drawn therefrom by the delivery device and administered to the patient through the delivery device.

Figure 7:
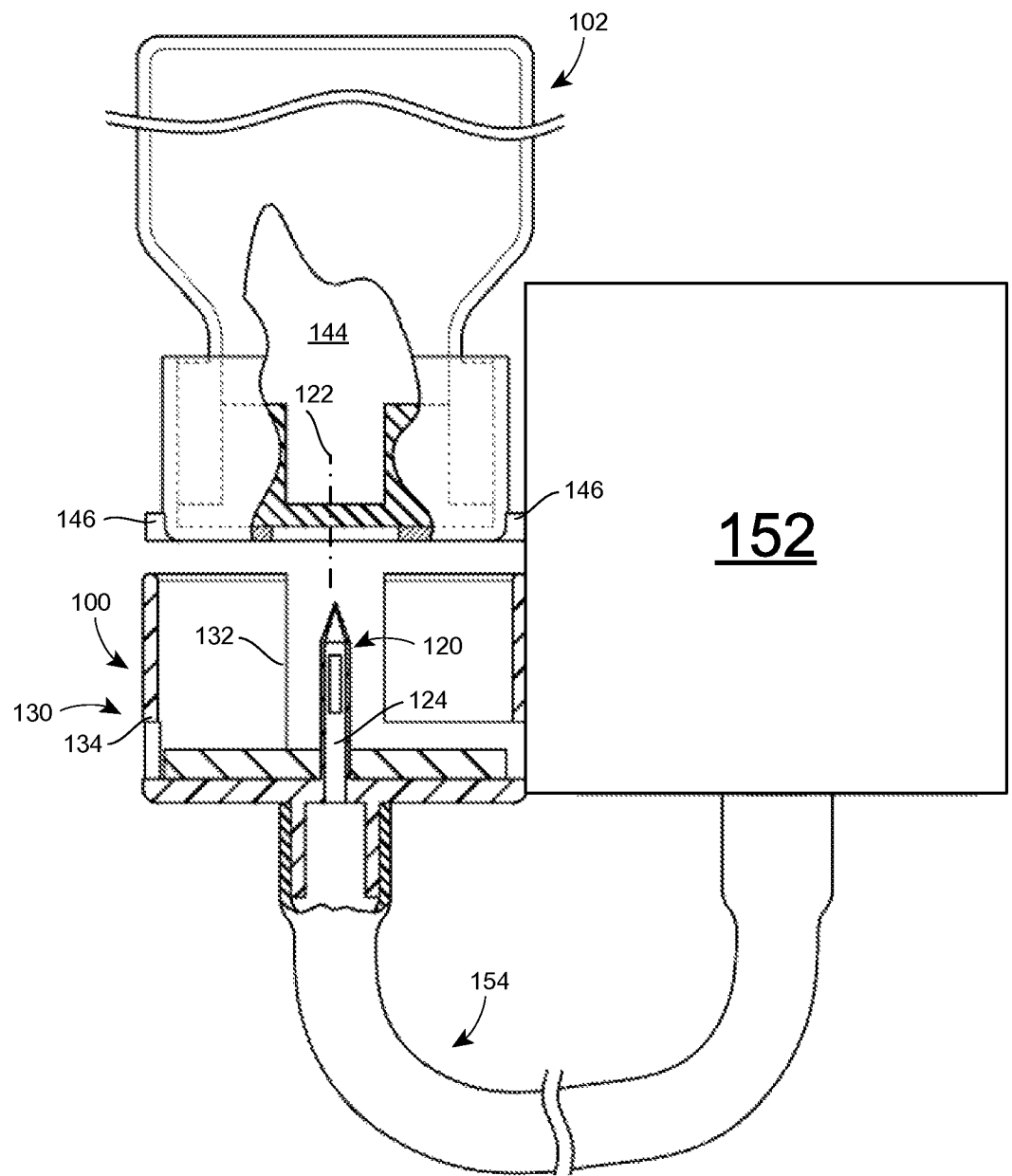
FIG. 7 is a cross-sectional view of the vial adapter of FIG. 1 taken about line 3-3 in FIG. 2, in combination with a machine and a vial shown in partial cross-section.

In this regard, the adapter 100 may be attached to or mounted on and may be used with medical equipment, represented schematically in the embodiment illustrated in FIG. 7 at 152. The medical equipment 152 may include a dialysis machine or other machine, and the adapter 100 may be attached to or mounted on the machine for convenience sake, so that the adapter 100 may be used with the machine to which it is attached or on which it is mounted, or with other equipment (including, by way of example and not limitation, machinery, peripherals, extension sets, administration sets, tubing, etc) associated with or in general physical proximity to the machine. When attaching or mounting the vial adapter 100 to the equipment 152, the vial adapter 100 may be held in place with hardware (for example, a clamp) attached to or mounted on the medical equipment (for example, the dialysis machine) and the vial 102 can then be inserted into the stationary adapter 100. According to the embodiment of FIG. 7, the vial adapter 100 is held in place on a device 152 with the spike 120 oriented toward the top of the page, which will be designated "up" or "upwards" for convenience sake. While the spike 120 may be oriented upwards, as is illustrated, it is also possible for the spike 120 to be oriented downwards instead, or even at some other orientation between "up" and "down."

According to one embodiment of the system illustrated in FIG. 7, the vial adapter 100 may be attached to or mounted on a dialysis machine, and may be used with a vial 102 containing an erythropoiesis stimulating agent (ESA), such as Epogen® or Aranesp®, for automated administration of the ESA using the dialysis machine. In such an embodiment, a medical professional may be able to insert a vial 102 into the vial adapter 100 and then allow the therapeutic to be administered with little or no additional intervention.

The vial adapter 102, as illustrated in FIG. 7, is used according to the following method. With the vial adapter 100 held in place on the medical equipment 152, the vial 102 may be generally aligned axially with the vial adapter 100, and in particular the spike 120. The vial 102 may then be rotated to align the tabs 146 with the first sections 132 of the slots 130, such as illustrated in FIG. 4. The vial 102 may then be advanced in the direction of the adapter 100, the tabs 146 cooperating with the first sections 132 of the slots 130 to guide the motion of the vial 102 so that it is primarily along the axis 122 of the spike 120. Therefore, the spike 120 will be advanced axially into the vial 102 so that the spike passage 124 is in fluid communication with the receptacle 144 of the vial 102. The spike passage 124 may also be in fluid communication with the equipment 152 via tubing 154.

To secure the vial adapter 100 to the vial 102, the vial 102 is rotated or twisted about the axis 122. According to one embodiment of the present procedure, the vial 102 is rotated or twisted until the tabs 146 traverse the entire length of the second sections 134 of the slots 130, such that the tabs 146 move along the section sections 134 between the state illustrated in FIG. 4 and the state illustrated in FIG. 5. The state illustrated in FIG. 4 may be referred to as the unlocked state, while the state in FIG. 5 may be referred to as the locked state. With the vial 102 in the locked state, the equipment 152 may automatically administer the contents of the vial 102 during the normal operation of the equipment 152.

Having thus described the structure and exemplary uses of the system including the vial adapter 100 and the vial 102 in general terms, the details of each of these elements in the embodiment of FIGS. 1-7 and the variants of FIGS. 8-18 are now discussed.

Returning to FIGS. 1 and 2, as mentioned above, the vial adapter 100 includes the base 110. As illustrated, the base 110 is a disk having a circular or near-circular shape. As will be recognized, it is not necessary for the base 110 to be circular or near-circular according to all embodiments. Moreover, the disk has a dimension along the axis 122 of the spike 120 that is significantly smaller than its dimensions in a plane in which the disk is disposed (for example, its diameter). It will also be recognized that this is not a requirement of the invention, but merely an aspect of the embodiment as illustrated.

The skirt 116 depends from the first side 112 of the base 110. As illustrated, the skirt 116 has a wall 160 that is generally annular in cross-section in a plane orthogonal to the longitudinal axis 122 of the spike 120. The wall 160 has an outer surface 162 and an inner surface 164, the inner surface 164 and a surface 166 of the base 110 cooperating to define the space 118 (see FIGS. 1 and 3). While the outer and inner surfaces 162, 164 are cylindrical as illustrated, it will be recognized that the inner and outer surfaces 162, 164 may have other geometries as well. Because of the cylindrical geometry of the vial 102, the cylindrical surfaces 162, 164 may be particularly well suited for use in various embodiments of the vial adapter 100 illustrated herein.

As mentioned above, the skirt 116 has at least one slot 130. As specifically illustrated, the skirt 116 includes two slots 130. As noted above, additional slots 130 may be included, or the slot 130 may even be removed altogether (see the embodiment illustrated in FIG. 15, for example). The illustrated slots 130 are identical in shape and structure, and are disposed at regular intervals (e.g., spaced by 180 degrees or opposite from each other) about the periphery of the skirt 116. According to other embodiments, the slots 130 may differ in shape or structure, and need not be disposed at regular intervals about the periphery of the skirt 116. Without wishing to be bound by a mechanism of operation, it is believed that regular intervals (for example, 180 degrees, 90 degrees, etc.) may facilitate better distribution of forces about the skirt 116.

It will be recognized that the first and second sections 132, 134 of the slot 130 each have first ends 170, 172 and second ends 174, 176. The first end 170 of the first section 132 is open, while the second end 176 of the second section 134 is closed. The second end 174 of the first section 132 is connected to the first end 172 of the second section 134.

Each slot 130 has an L-shaped profile, with the first and second sections 132, 134 of each slot 130 connected at right angles to each other. That is, to the extent that the first section 132 of the slot 130 is parallel to the longitudinal axis 122 of the spike 120, the second section 134 lies in a plane that is orthogonal to the longitudinal axis 122. Alternatively, the first and second sections 132, 134 may be disposed at non-right angles to each other, such that the second section 134 has an upward or a downward slant relative to the first section 132.

Moreover, in the first and second sections 132, 134 of the slots 130 are of uniform width as illustrated. That is, to the extent that the first section 132 of the slot 130 is defined by edges 180, 182, the edges 180, 182 are spaced by an equal distance from each other continuously from the first end 170 to the second end 174 of the section 132. Similarly, the second section 134 of the slot 130 is defined by edges 190, 192 that are spaced by an equal distance from each other from the first end 172 to a second end 176 of the section 134. Alternatively, the distances may vary continuously or discontinuously along the edges 180, 182, 190, 192. Certain embodiments illustrated in FIGS. 9-13 illustrate certain embodiments where the distances vary over particular regions of the edges to define regions of non-uniform width, the purpose and function of these regions explained in detail below.

The second sections 134 of the slots 130 may extend about the longitudinal axis 122 in a single direction about the longitudinal axis 122, as best illustrated in FIGS. 1, 4 and 5. This facilitates the use of a simple rotating or twisting motion in a single angular direction to engage the tabs 146 in the slots 130, as will be explained in detail below. It is possible for the slots 130 to instead depend in either direction from the first section 132, permitting the tabs 146 to engage in the slots 130 without regard for the angular direction (clockwise or counterclockwise) of the rotating or twisting motion.

As illustrated in the embodiment of FIGS. 1-6, the slots 130 extend through the wall 160 of the skirt 116 from the outer surface 162 to the inner surface 164. This facilitates use of tabs 146 that may depend beyond the outer surface 162, thereby providing a visible indication of the degree to which the vial adapter 100 and the vial 102 have been engaged with each other. However, it will be recognized that the slots 130 need not extend through the wall 160 from the inner surface 164 to the outer surface 162. The slots 130 could extend to a depth within the wall 160 that is smaller than the width of the wall 160. Such an embodiment may require a thicker wall 160 than is illustrated to accommodate a slot 130 of suitable depth for a particular application, but it will be recognized that the relative depth of the slot 130 and the thickness of the wall 160 may be selected according to the circumstances of a particular embodiment.

As noted above, the spike 120 depends from the first side 112 of the base 110 into the space 118. The spike 120 illustrated in FIGS. 1-6 has a generally tubular, cylindrical shaft 200 that ends in a solid, conical head 202 as best seen in FIG. 4. The spike 120 has a passage 124, which passage 124 may be defined by an inner surface 204 of the tubular shaft 200. The passage 124 may be in fluid communication with at least one aperture 206 that is formed in the spike 120; in the illustrated embodiment of FIGS. 1-6, two apertures 206 are formed in the shaft 200 and extend through a wall 208 of the shaft 200 between the inner surface 204 and an outer surface 210. The two apertures 206 are disposed opposite each other across the longitudinal axis 122 of the spike 120 (see FIG. 1). In various embodiments, more than two apertures 206 may be present in the shaft 200.

As will be recognized with reference to FIGS. 8-15, the shape of the spike 120 may vary considerably, relative to the size and shape of the shaft 200 and the head 202, as well as the placement of the apertures 206. It will also be recognized that the spike 120 may be made of materials different than are used to form the remainder of the vial adapter 100. These variants will be discussed in greater deal below.

As is also illustrated in FIGS. 1-6, vial adapter 100 may include a biasing mechanism 220. The biasing mechanism 220 may be in the form of a resilient pad or elastomer disposed about the spike 120 and depending into the space 118, and in particular into the space 118 in the direction of the end or tip of the spike 120. This resilient pad or elastomer 220 may be in the form of a disk having an annular shape as viewed along the longitudinal axis 122 of the spike 120, although this is a non-limiting example. The shape and thickness (as measured in a dimension along the longitudinal axis 122 of the spike 120) of the resilient pad 220 may vary in other embodiments. The biasing mechanism may also be in the form of a spring (such as a coil or leaf spring) instead. According to certain embodiments, such as the embodiment illustrated, the biasing mechanism 220 may be attached to the base 110 of the adapter 100 about the spike 120, although this need not be the case in all embodiments.

If the biasing mechanism 220 has been included, as has been illustrated in FIGS. 1-6, the biasing mechanism 220 will exert a force on the first end 142 of the vial 102 in a direction away from the base 110 of the adapter 100, which may cause misalignment between the tabs 146 and the second section 134 of the slot 130 during insertion of the vial 102 in the adapter 100. A counter force may be required to permit the alignment of and movement of the tabs 146 in the second sections 134 of the slots 130. It will be recognized that when the axial force applied to the adapter 100 in the direction of the vial 102 is removed, the biasing mechanism 220 will encourage the tabs 146 to cooperate with the skirt 116 to inhibit movement of the tabs 146 along the second section 134 of the slot 130.

In the particular embodiment of FIGS. 1 and 2, the apertures 206 have an elongated shape with first and second ends 230, 232 that are axially spaced from each other (see FIG. 1). Without wishing to be bound by a mechanism of operation, it is believed that the elongated shape of the apertures 206 facilitates removal of the entire product from the vial 102. However, it will be recognized that the apertures 206 may have other shapes as well.

As noted above, these structures of the vial adapter 100 cooperate with the vial 102, which is now described in detail with reference to FIGS. 3 and 6.

The vial 102 includes a container 240 with an inner surface 242 that defines the receptacle 144. The container 240 may be made of glass, for example. The container 240 has a first open end 244 at the first end 140 of the vial 102, and a second closed end 246 at the second end 142 of the vial 102. While the container 240 as shown has a single wall 248 that defines the first and second ends 244, 246, the first and second ends 244, 246 may be formed separately so that the second end 246 may be moveable relative to the first end 244 of the container 240.

The vial 102 also includes an exemplary sealing assembly 250 disposed over the open end 244, the sealing assembly 250 including a stopper 252 and a seal 254. The stopper 252 has a first surface 256 facing the first end 244 of the container 240, and a second surface 258 facing a first end 260 of the seal 254. The seal 254 includes a first rim 262 disposed about the first end 260 of the seal 254, which abuts the second surface 258 of the stopper 252, and a second rim 264 disposed at a second end 266 of the seal 254 that is disposed about a rim 268 formed at the first end 244 of the container 240 to hold the sealing assembly 250 in place on the container 240.

Extending from the seal 254 of the vial 250 are the tabs 146. As will be recognized with reference to FIGS. 16 and 17, the tabs 146 may extend from the seal 254 according to any of a number of different structural devices, including being formed (e.g., molded) as a single unit with the seal 254, carried on separate structures that are fastened to or about the seal 254, etc. As illustrated in FIGS. 4 and 5, the tabs 146 as illustrated lie along an axis 270 so that the tabs 146 are disposed 180 degrees from each other, or opposite across from each other. It is possible to vary this spatial distribution of the tabs 146 about the first end 140 of the vial 102, as noted above. In addition, while the tabs 146 have a cross-section that is rectangular in a plane orthogonal to the axis 270, as is illustrated below in FIGS. 8-14 the cross-section of the tabs 146 may vary as well.

As noted above, the purpose of the vial adapter 100 is to connect the vial 102 to a secondary device, machine or system. Consequently, in various embodiments, the adapter 100 includes the connector 126, which is adapted to attach to the device or system. The connector 126 may have a wall 280 with an exterior surface 282 that is threaded. Similarly, the syringe 150 may have a collar 284 with an interior surface 286 that is threaded. By engaging the threaded surfaces 282, 286, the syringe 150 may be secured to the connector 126. With the syringe 150 secured to the connector 126, a passage 290 of a luer tip 292 of the syringe 150 may be in fluid communication with the passage 128 of the connector 126 and/or the passage 124 of the spike 120. In other embodiments, however, the connector 126 may have an exterior surface 282 that is not threaded.

As noted above with reference to the details of the embodiment of FIGS. 1-6, there are a large number of variants possible. Certain of these variants are illustrated in FIGS. 8-17.

Figure 8:
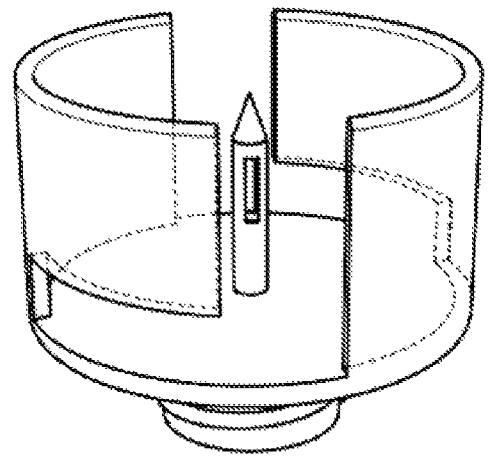
FIG. 8 is a perspective view of a vial adapter according to a first alternative embodiment.

For example, in the variant of FIG. 8, the embodiment is similar in detail to the embodiment of FIGS. 1-6 as to the base, skirt, spike and connector. However, unlike the embodiment of FIGS. 1-6, no biasing mechanism is provided. According to such an embodiment, it is not necessary to apply an axial force to the vial when rotating the adapter relative to the vial to secure the adapter to the vial. Of course, it is also true that the biasing mechanism is not available to apply a force to encourage the tabs of the vial into engagement with the slot to discourage movement of the tabs relative to the slot in the locked state.

FIGS. 9-13 illustrate additional variants that differ according to one aspect relative to the embodiment in FIGS. 1-6 in that the variants do not have first and second sections of the corresponding slots that are of uniform width from one end to the other. In particular, the embodiments of FIGS. 9-13 illustrate variants that include a slot in the skirt that has a second section with at least a region wherein the width is greater over some portion of that region than it is in the remainder of the section of the slot. As illustrated, these regions of greater width define geometric shapes that may conform to a tab attached to a vial, for example to differentiate one vial containing a specific composition from another vial containing a different composition.

Figure 9:
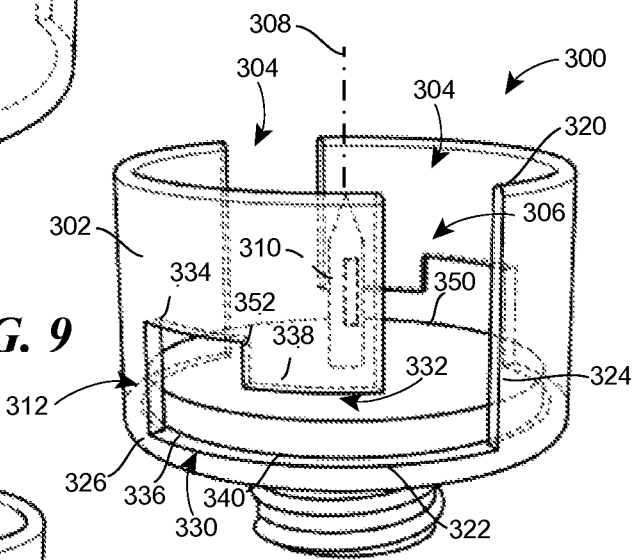
FIG. 9 is a perspective view of a vial adapter according to a second alternative embodiment.

For example, FIG. 9 is an embodiment of a vial adapter 300 with a skirt 302 having two slots 304. Each slot 304 may have a first section 306 that extends parallel to a longitudinal axis 308 of a spike 310, and a second section 312 extending in an arc about the longitudinal axis 308 and connected to the first section 306.

It will be recognized that the first and second sections 306, 312 of the slots 304 each have first ends 320, 322 and second ends 324, 326. The first end 320 of the first section 306 is open, while the second end 326 of the second section 312 is closed. The second end 324 of the first section 306 is connected to the first end 322 of the second section 312.

Each slot 304 has an J-shaped profile, with the first and second sections 306, 312 of each slot 304 connected at right angles to each other. The J-shape of the slot 304 is caused by the fact that the second section 312 has a region 330 that has a width that is larger than a remainder 332 of the section 312 of the slot 304. In particular, the region 330 the second section 312 of the slot 304 is defined by edges 334, 336, the edges 334, 336 are spaced by an equal distance from each other continuously from one end to the other end of the region 330. Similarly, the remainder 332 of the second section 312 is defined by edges 338, 340 that are spaced by an equal distance from each other from one end to the other end. However, the distance between the edges 334, 336 is larger than spacing between the edges 338, 340.

Because of the varying widths of the second section 312 of the slots 304 in FIG. 9, the region 330 of the section 312 appears to have a rectangular shape. This rectangular shape may conform to that of the cross-section of the tab 146 of the vial 102, such as is illustrated in FIGS. 3-6. When used in combination with a biasing mechanism 350, as illustrated, and when the axial force is removed from the adapter 300 during the assembly procedure, the tabs 146 will be move into the region 330, thereby providing an even more secure attachment between the vial adapter 300 and the vial 102 in that the movement of the tabs 146 will be resisted by the axially-oriented wall 352.

Figure 11:
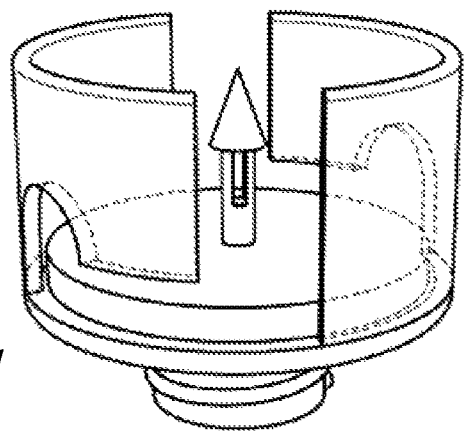
FIG. 11 is a perspective view of a vial adapter according to a fourth alternative embodiment.
Figure 12:
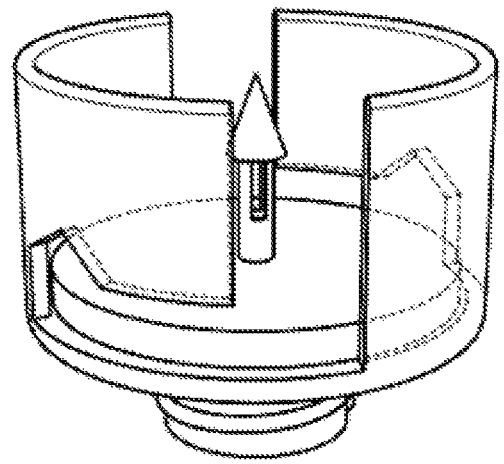
FIG. 12 is a perspective view of a vial adapter according to a fifth alternative embodiment.
Figure 13:
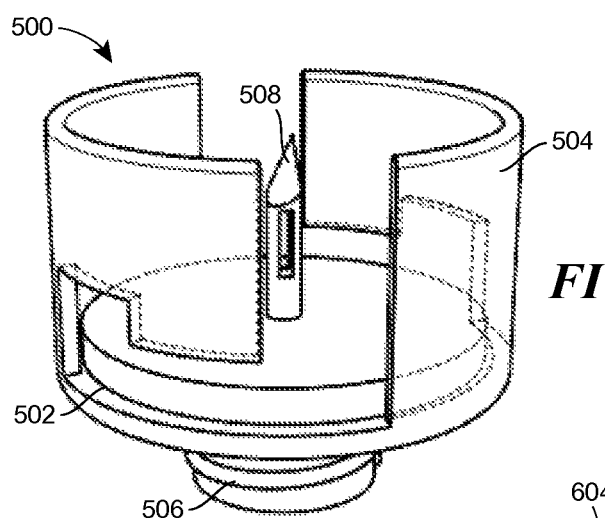
FIG. 13 is a perspective view of a vial adapter according to a sixth alternative embodiment.

It will be recognized that a similarly shaped slot with rectangular region is illustrated in FIGS. 10 and 13. It will also be recognized that variants are possible, for example, where the width of the second section of the slot in the region of greater width is not uniform (i.e., continuously the same distance between opposing edges), but varies. For example, as illustrated in FIGS. 11 and 12, different geometric shapes may be defined, such as a semi-circle or a triangle, where the width of the region of greater width varies. It will also be recognized that if vials are used having tabs of different cross-section, a visual and/or tactile warning may be provided to the user if the vial having a particular cross-section is used with an adapter that has a slot that is does not have a mating or conforming shape (e.g., a tab of rectangular cross-section being used with a slot having a region of semicircular shape).

FIGS. 10-13 also illustrate variants that differ according to another aspect relative to the embodiment in FIGS. 1-6 in that the variants of FIGS. 10-13 include a different spike. For example, in the embodiments of FIGS. 10-12, the vial adapters have a spike with a head with a cross-section in plane orthogonal to a longitudinal axis that is larger than a cross-section of the shaft, while the vial adapter in FIG. 13 has a spike that is not formed as one piece (i.e., integrally with) with the base, skirt and connector.

Turning first to FIG. 10, an adapter 400 includes a spike 402 with a shaft 404 and a head 406. As mentioned above, the spike 402 differs from the spike 120, for example, in that the head 406 has a cross-section in a plane orthogonal to a longitudinal axis that is larger than a cross-section of the shaft 404. As will be recognized, the cross-section of the head 406 is not larger than the cross-section of the shaft 404 at all points along an axis 408 of the spike 402. Instead, the head 406 has at least one cross-section that defines a surface 410 that faces a surface 412 of a base 414 of the adapter 400.

The surface 410 may be used to further secure the vial 102 to the adapter 400. That is, once the spike 402 has been advanced into the stopper 252, the stopper 252 will be disposed between the facing surfaces 410, 412, and the surface 410 will inhibit the relative movement of the vial 102 and the adapter 400 along the axis 408. The surface will act on the inner surface of the stopper 252 to inhibit relative movement of the vial 102 and the adapter 400 along the axis 408 even before the adapter 400 is rotated or twisted relative to the vial 102 to engage the tabs 146 in slots 420 in skirt 422.

Figure 15:
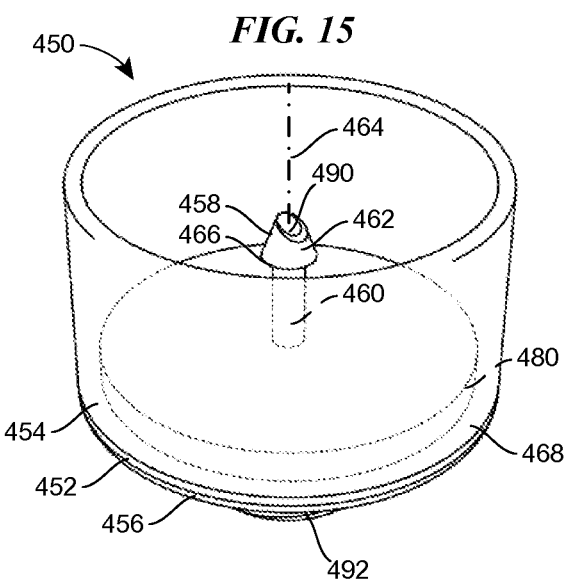
FIG. 15 is a perspective view of a vial adapter according to an eighth alternative embodiment.

Along similar lines, FIG. 15 illustrates an embodiment of an adapter 450 that does not include slots in the skirt (and consequently does not require tabs on the vial), but instead uses a spike having a head with a cross-section in a plane orthogonal to its longitudinal axis that is larger than a cross-section of the shaft to secure the adapter 450 to a vial. In particular, the vial adapter 450 includes a base 452 having first and second opposing sides 454, 456, and a spike 458 that depends from the first side 454 of the base 452. The spike 458 has a shaft 460 connected to the base 452 and a head 462 connected to the shaft 460, the head 462 having a cross-section in a plane orthogonal to a longitudinal axis 464 of the spike 458 that is larger than a cross-section of the shaft 460. The at least one cross-section defines a surface 466 that faces a surface 468 of the base 452 of the adapter 450.

To assist in holding the stopper of the vial against the surface 466, a biasing mechanism 480 is disposed about the spike 458 on the surface 466. As illustrated, the biasing mechanism 480 is in the form of a resilient pad. The pad 480 provides a force along the axis 464 to urge a stopper disposed between the opposing surfaces 466, 468 against the surface 466. In doing so, the inner surface of the stopper would be held against the surface 466.

The spike 458 is also provided with an aperture 490 disposed along the axis 464. The aperture 490 is in fluid communication with a passage that runs through the spike 458. The passage that runs through the spike 458 is, in turn, in communication with a passage that runs through a connector 492 that is disposed on the second side 456 of the base 452. With the stopper urged against the surface 466 of the spike 458, the aperture 490 will be disposed in such a fashion as to permit, assist or encourage almost the entire contents of the vial to pass through the adapter 450.

In comparing the spikes 402, 458, it will be recognized that the shape of the head 406, 462 varies, between that of a conical sectional and a truncated conical section. However, the embodiments according to this variant are not limited to only conical shapes. For example, the head may have the shape of a pyramid or truncated pyramid instead, or may be substantially triangular in shape. Other variants are possible.

As mentioned previously, a still further embodiment of a spike that may be used with the adapters discussed herein is illustrated in FIG. 13. According to this embodiment, an adapter 500 includes a base 502, skirt 504, and connector 506 that are formed (e.g., molded) as a single unit, from polycarbonate, for example. In addition, the adapter 500 includes a spike 508 that made from metal, for example in the form of a sharp-pointed metal cannula. The metal spike 508 may be attached to the base 502 using an adhesive, for example, or by molding the base 502 about and end of the spike 508. Otherwise, the embodiment is similar to, for example, the embodiment illustrated in FIG. 9.

Figure 14:
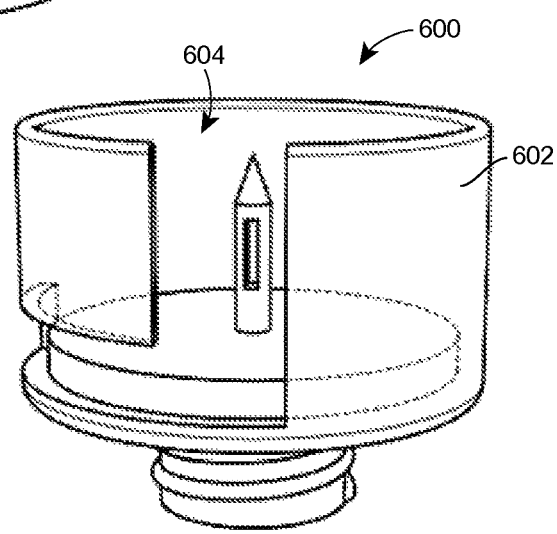
FIG. 14 is a perspective view of a vial adapter according to a seventh alternative embodiment.

As a still further variant, an adapter 600 is illustrated in FIG. 14. Unlike the adapters illustrated in FIGS. 1-13, the adapter 600 has a skirt 602 with a single slot 604. The slot 604 is similar in other regards to the slot 130 of the adapter 100 in FIGS. 1 and 2, for example. While two or more regularly spaced slots, such as are illustrated in FIGS. 1-13 may assist to balancing the forces on the tabs 146 to a greater degree, it is believed, without wishing to be bound by a mechanism of operation, that even the use of a single slot 604 may still provide advantages according to the present disclosure.

Figure 16:
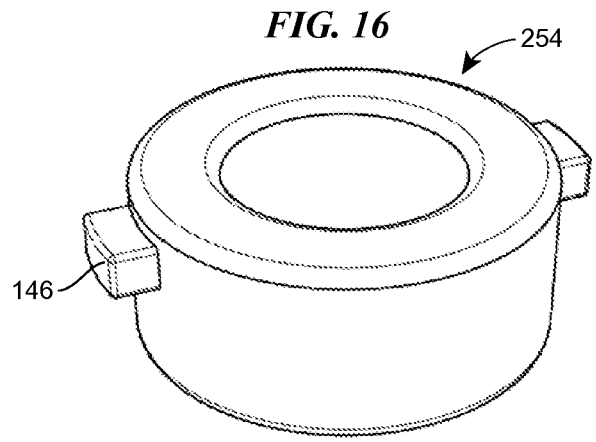
FIG. 16 is a perspective view of a seal for use with the vial illustrated in FIG. 3.
Figure 17:
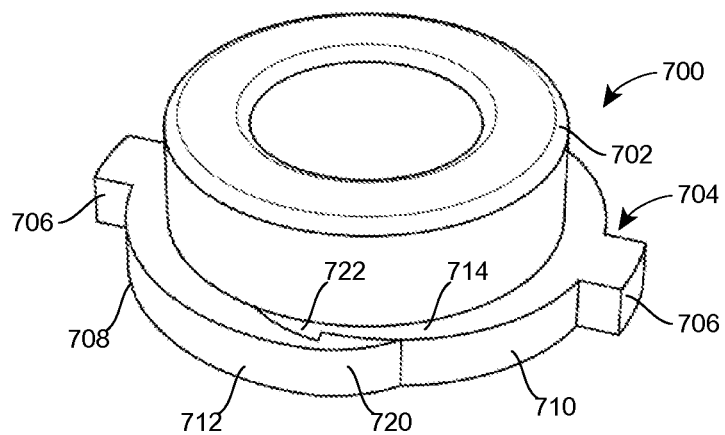
FIG. 17 is a perspective view of an alternative seal for use with the vial illustrated in FIG. 3.

In a final note regarding variants in regard to the present disclosure, FIGS. 16 and 17 illustrate different embodiments of the seal used with the adapters and vials illustrated in the Figures.

FIG. 16 illustrates the seal 254 of FIGS. 3 and 6, wherein the tabs 146 are formed (e.g., molded) as a single piece with the remainder of the seal 254, from polycarbonate for example. It will be recognized that the tabs 146 may also be formed by deforming the wall of a conventional metal seal as well. It will also be recognized that the tabs 146 may be formed separately from the remainder of the seal, and then attached in a separate step.

FIG. 17 illustrates a further option for securing tabs to a seal. According to this embodiment, the seal 700 includes two portions: a first collar 702 that would fit over and around a first end of a container and a stopper, similar to the seal 254 illustrated in FIG. 1, and a second collar 704 that would be disposed about the first collar 702 and carry tabs 706 adapted to cooperate with any of the vial adapters illustrated in FIGS. 1-13. Specifically, the second collar 704 includes two separate arcs 708, 710 that are joined together at their ends 712, 714 to define the collar 704. As illustrated, each arc 708, 710 carries one of the tabs 706, although according to other embodiments, only one arc 708, 710 may carry a tab 706 (for use with the embodiment illustrated in FIG. 14, for example), or each arc 708, 710 may carry more than one tab 706.

Each arc 708, 710 may also include a fastener 720, 722 used to secure the ends 712, 714 of the arcs 708, 710 together. As illustrated, the fasteners 720, 722 define a pair of interlocking hooks, which hooks secure the ends 712, 714 together to secure the collar 704 to the collar 702. It will be recognized that other variants are possible, including a variant wherein the arcs 708, 710 are integrally formed (e.g., molded as a single unit) at one of the junctions between the ends 712, 714, and the other junction has ends 712, 714 with fasteners 720, 722. For that matter, the ends 712, 714 may be secured to each other through a more permanent joining process (e.g., ultrasonic welding) once the arcs 708, 710 are in position, rather than include mating fastener pairs. Further, the hook fasteners illustrated are simply an exemplary embodiment for the fasteners 720, 722, which may take other forms as well.

It will be recognized that while tabs 146 or 706 are illustrated as being rectangular in shape in FIGS. 16 and 17, the shape may vary in other embodiments of the seal depending on the shape of the slot or slots in the vial adapter.

Figure 18:
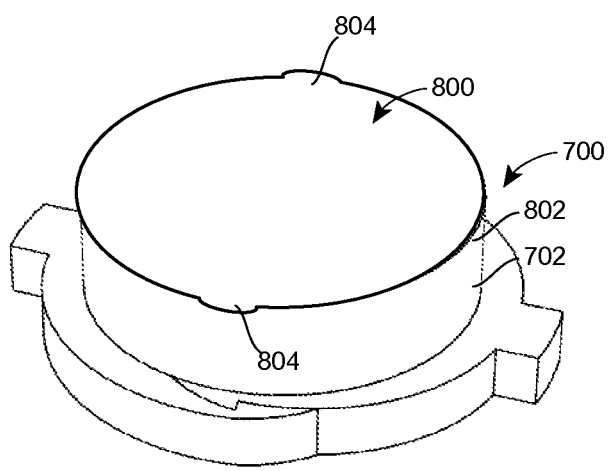
FIG. 18 is a perspective view of the seal illustrated in FIG. 17 in combination with a cap.

It will also be recognized that any of the seals illustrated herein may be used in conjunction with a cap or lid, as is illustrated in FIG. 18. In particular, the seal 700 has a cap or lid 800 disposed over the seal 700 at a first end 802 of the collar 702. This cap 800 may be attached to the stopper (not shown) associated with the seal 700, or it may be attached to the seal 700 directly. Prior to use, the cap 800 is removed from the seal 700, by placing an edge of a thumb or finger under one of two illustrated flaps 804, and applying an upward (as illustrated in FIG. 18) force to the flap 804 to "flip" the cap 800 off of the seal 700. With the cap 800 removed, the vial associated with the seal 700 may be used with the vial adapter 100, as explained in detail above.

Figure 19:
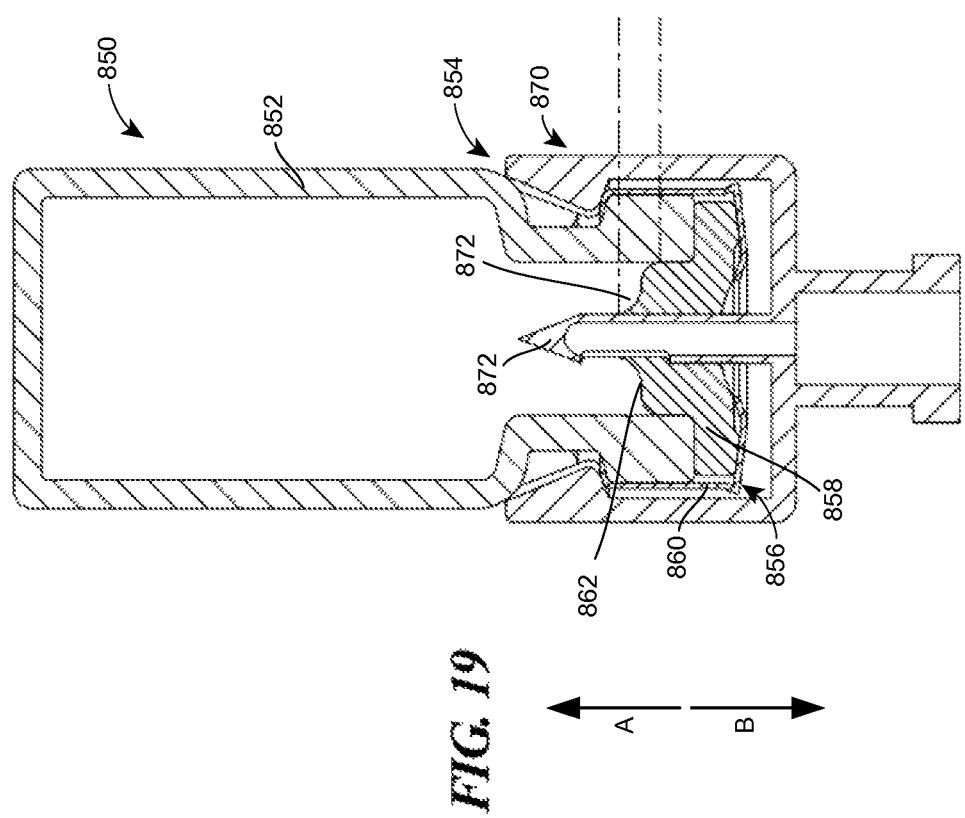
FIG. 19 is a cross-sectional view of a spike of a vial adapter advancing into a stopper of a vial to access material inside the vial, with a trapped residual volume defined by deflection of the stopper.

Aspects of the above-mentioned embodiments may be combined to address a further issue involved with the use of adapters used to connect syringes, lines and the like to vials, such as those illustrated herein, where the adapter is designed to be advanced into a stopper that closes off the open end of the vial. The issue that can arise with the use of such adapters is illustrated in FIG. 19.

A vial 850 includes a container 852 with an open end 854. The vial 850 also includes a sealing assembly 856 disposed over the open end 854, the sealing assembly 856 including a stopper 858 and a seal, or crimp ring, 860. The stopper 858 has an inner surface 862. Attached to the vial 850 is a vial adapter 870 having a spike 872 that advances into the stopper 858 as the spike is advanced in the direction of arrow A.

As illustrated, when the spike 872 of the vial adapter 870 advances into the stopper 858, the inner surface 862 of the stopper 858 is displaced from a first position to a second position, at least in the immediate region surrounding the spike 872. The displacement of the inner surface 862 causes an annular volume 874 to form about the spike 872, which volume cannot be accessed by the spike 872. Even after the remainder of the contents of the container 852 have been drained from the container 852 (and hence the vial 850), some portion of the contents may remain trapped in the annular volume 874, and may be referred herein to as a trapped residual volume.

It has been determined that one way to address the displacement of the inner surface 862 is to withdraw the spike 872 in the direction of arrow B. The motion of the spike 872 in the direction of arrow B causes movement of the stopper 858, and in particular the inner surface 862, back to the neutral position. Of course, if the spike 872 is withdrawn too far, the spike 872 may become occluded by the stopper 858, or may even permit material to leak from the container 852. If the contents of the vial 850 are very expensive, such that it is advantageous and/or highly desirable to access even the trapped residual volume, then a less than optimal draining of the vial 850 caused by occlusion of the spike 872 or losses through leakage are to be avoided.

As consequence, FIGS. 20-61 illustrate a number of vial adapters that include features for controlled withdrawal of the spike associated with the vial adapter after advancing into the vial stopper by the spike. The controlled withdrawal is intended to prevent occlusion of the spike by the stopper if the distance of the withdrawal is too great, and also to prevent leakage from the combination of the vial adapter and vial.

To this end, a number of the alternative vial adapters include a biasing mechanism, often in the form of spring, similar to those vial adapters discussed above. See FIGS. 20-31. Consequently, while the distance traveled by the spike in the illustrations of FIGS. 20-31 may appear larger that the distance traveled in the illustrations of FIGS. 1-18, there may be commonality of structure and action on this point between the embodiments.

Furthermore, although many of the embodiments of the vial adapters in FIGS. 20-61 may include one or more radially, inwardly directed protrusions, tabs, or hooks, which grip an end of the vial to prevent separation of the vial adapter from the vial, it will be recognized by one skilled in the art that the slot-and-tab mechanism for locking the vial adapter to the vial in the embodiments in FIGS. 1-18 may be substituted therefor. In this regard, it is particularly noted that the slot-and-tab mechanism would also permit for the spike to be withdrawn in a direction away from the vial after advancing into the vial stopper by the vial adapter spike. Consequently, while the substitution of the slot-and-tab mechanism is not illustrated in substitution for the radially, inwardly directed protrusions and the like, such a substitution is possible and within the scope of the present disclosure. In fact, in those instances where the vial adapter is rotated about the axis of the vial adapter spike, the slot-and-tab arrangement discussed above may be of particular interest for limiting the distance of withdrawal of the spike from the vial.

Furthermore, it will be recognized that having a separately formed spike for the vial adapter is contemplated by the embodiments of FIGS. 1-18. As such, the separation of the vial adapter spike from the remainder of vial adapter may be more apparent in the embodiments of FIGS. 20-61, the separation is one of degree, rather than completely different in kind.

Starting then with the variant illustrated in FIGS. 20-22, and turning first to FIG. 20, it will be recognized that a vial 900 and a vial adapter 902 (which may also be referred to as a vial adapter assembly) are illustrated prior to the vial adapter 902 being attached to the vial 900. While the vial 900 and vial adapter 902 are illustrated with the vial adapter 902 disposed above the vial 900, this should not be taken as a limitation of the use of the vial adapter 902 with the vial, for the combination could have as easily been illustrated in the orientation illustrated in FIG. 19, or at any angle between these orientations. This is true of the other illustrations of the embodiments of FIGS. 20-61.

The vial adapter 902 includes a base 910 having first and second opposing sides 912, 914 (see FIGS. 21 and 22 as well). A tubular skirt 916 may depend from the first side 912 of the base 910, the tubular skirt 916 bounding a space 918 to receive the vial 900. A spike 920 may depend from the first side 912 of the base 910 into the space 918. The spike 920 may have a longitudinal axis 922 and a spike passageway 924 (see FIGS. 21 and 22). The vial adapter 902 may also include a connector 926 disposed on the second side 914 of the base 910, the connector 914 having a connector passageway 928 that is in fluid communication with the spike passageway 924 (see FIGS. 21 and 22). The base 910, skirt 916, spike 920 and connector 926 may be formed (e.g., molded) as a single unit out of polycarbonate, for example.

The vial adapter 902 also includes a biasing mechanism 930, in the form of a conical coil spring. While the biasing mechanism 930 is illustrated separated from the remainder of the vial adapter 902 in FIG. 20, the biasing mechanism would typically inserted into the space 918 prior to the vial adapter 902 being attached or connected to the vial 900. In particular, the vial adapter 902 may include a cylindrical platform 932 that depends from the side 912 of the base 910, and an end 934 is received about the platform 932 so as to grasp the platform 932 about its periphery and thereby attach the spring 930 to the remainder of the vial adapter 902. A second end 936 of the spring 930 cooperates with a surface 938 of the vial 900 as will be explained relative to FIGS. 21 and 22.

The vial adapter 902 also includes a plurality of inwardly, radially directed protrusions, projections or tabs 940. The tabs 940 each have a surface 942 that cooperates with a surface 944 of the vial 900 opposite the surface 938 to prevent separation of the vial adapter 902 from the vial 900. However, as will be explained in regard to FIGS. 21 and 22, the distance between the surface 912 of the base 910 and the surfaces 942 of the tabs 940 is such that the surfaces 942, 944 do not come in contact with the spring 930 fully compressed.

The operation of the vial adapter 902 is now discussed relative to the illustrations of FIGS. 21 and 22. Initially, the vial adapter 902 is advanced in the direction of arrow A in FIG. 21 such that the spike 920 comes in contact with a stopper 950 of the vial 900. At this time, the protrusions 940 come in contact with a crimp ring 952 that holds the stopper 950 in place on the vial 900. The cooperation between the protrusions 940 and the crimp ring 952 forces the skirt 916 of the vial adapter 902 radially outward, until the spike 920 is advanced into the stopper 950 to such an extent that the protrusions 940 are received within the neck 954 of the vial 900 (see FIG. 20), this section of the vial 900 being smaller in diameter that the section about which the crimp ring 952 is disposed. At this point, the skirt 916 moves radially inwardly. The spring 930 is partially or fully compressed between the surfaces 912, 938 of the vial adapter 902 and the vial 900, respectively.

As will be recognized relative to FIG. 21, there is a gap in the longitudinal direction between the surfaces 942, 944 of the vial adapter 902 and the vial 900 with the spring 930 compressed as in FIG. 21. The size of the gap will be selected according to the desired motion of the vial adapter 902 so as to withdraw the spike 920 the desired distance from the stopper 950 to cause the stopper 950, and in particular a surface 958, to assume a shape similar to that as in the relaxed state, i.e., prior to the spike 920 advancing into the stopper 950. As illustrated in FIG. 22, when the downward force represented by the direction of the arrow A in FIG. 21 is removed, then the spring 930 applies an upward force represented by the direction of the arrow B in FIG. 22. This upward force moves the vial adapter 902 in the direction of the arrow B until the surfaces 942, 944 abut, at which point further motion in the direction of the arrow B is prevented.

The embodiments of FIGS. 23-31 share a commonality with the embodiment of FIGS. 20-22 in that all of these embodiments utilize a biasing mechanism or spring to provide a biasing or return force to move the vial adapter, or that portion of the vial adapter associated with the spike, away from the vial, and consequently away from the stopper. However, even a brief inspection of the figures will evidence the variety among the embodiments as to the placement of the biasing mechanism, and the manner in which the biasing or return force may be applied to the spike to move it away from the stopper.

Similar to FIG. 21, FIG. 23 illustrates a system including a vial 980 and a vial adapter 982 (which may also be referred to as a vial adapter assembly) prior to the vial adapter 982 being attached to the vial 980. While aspects of the vial adapter 982 have been separated into physically divisible and separable sections, the operation of the vial adapter 982 is generally the same as that of the vial adapter 902 illustrated in FIGS. 20-22. That is, the vial adapter 982 includes a biasing mechanism 984 (in the form of a coil spring) that applies a biasing or return force to the remainder of the vial adapter 902 to move a spike 986 associated with the vial adapter 902 away from the vial 900, and cause a stopper 988 associated with the vial 900 to deflect to limit or prevent a trapped residual volume from forming.

As to the structure of the vial adapter 982, the vial adapter 982 includes two subassemblies 1000, 1002, in addition to the spring 984.

The first subassembly includes the tubular skirt 1004 that depends from a first end 1006 to a second end 1008, the tubular skirt 1004 bounding a space 1010 to receive the vial 980. Attached to the skirt 1004 are a plurality of inwardly, radially directed protrusions, projections or tabs 1012. The tabs 1012 each have a surface 1014 that cooperates with a surface 1016 of the vial 982 to prevent separation of the vial adapter 982 from the vial 980 similar to surfaces 942, 944 of the variant of FIGS. 20-22.

The second subassembly 1002 includes a base 1020 with a first side 1022 and a second side 1024, the spike 986 depending from the first side 1022 and a connector 1026 depend from the second side 1024. The spike 986 and the connector 1026 may both have passageways 1028, 1030 (see FIG. 24). The second subassembly 1012 may also include a platform 1032 about the periphery of which an end 1034 of the biasing mechanism 984 is received. The base 1020, spike 986, connector 1026, and platform 1032 may be formed (e.g., molded) as a single unit out of polycarbonate, for example.

The embodiment of FIGS. 26-28 is in most respects similar to that of the embodiment of FIGS. 23-25. As such, a common numbering system has been utilized for the embodiment of FIGS. 26-28, except that the reference numerals used for the embodiment of FIGS. 26-28 are followed with primes. In particular, it will be recognized that the vial assembly 982' of the embodiment of FIGS. 26-28 is similar to the vial assembly 982 of FIGS. 23-25 in that the vial assembly 982' includes first and second subassemblies 1000', 1002' and a biasing mechanism 984', which collectively define the vial assembly 982'.

The difference is in regard to the structure and operation of the biasing mechanism 984'. Unlike the biasing mechanisms of FIGS. 20-25, the biasing mechanism 984' is not a coil spring. Instead, the biasing mechanism 984' is a more in the nature of a spring washer or a leaf spring, with multiple flexible legs that deflect under compression and then return to their original orientation to provide the biasing or return force.

FIGS. 29-31 illustrate a further variant of the embodiments of FIGS. 20-28 including a spring to provide a biasing or return force to automatically withdraw an associated spike a given distance from a stopper. Similar to the embodiment of FIGS. 20-22, and thus different from the embodiments of FIGS. 23-28, the embodiment of FIGS. 29-31 has a single assembly that includes skirt, spike, and connector. However, a second assembly is also included that cooperates with the first assembly (and thus both assemblies may be referred to as subassemblies) to define the embodiment of the vial adapter in FIGS. 29-31.

To begin then with FIG. 29, a vial 1060 and a vial adapter 1062 are illustrated. The vial adapter 1062 includes a first subassembly 1064, a second subassembly 1066, and a biasing mechanism 1068 (in this case in the form of a coil spring). As seen in FIGS. 30 and 31, the vial adapter 1062 is disposed about the vial 1060 when fully assembled, and thus the exploded view of FIG. 29 is for illustration and discussion purposes only.

The first subassembly 1064 includes a base 1070 having first and second opposing sides 1072, 1074 (see FIGS. 30 and 31 as well). A tubular skirt 1076 may depend from the first side 1072 of the base 1070, the tubular skirt 1076 bounding a space 1078 to receive the vial 1060. A spike 1080 may depend from the first side 1072 of the base 1070 into the space 1078. The spike 1080 may have a longitudinal axis 1082 (see FIG. 29) and a spike passageway 1084. The vial adapter 1072 may also include a connector 1086 disposed on the second side 1074 of the base 1070, the connector 1074 having a connector passageway 1088 that is in fluid communication with the spike passageway 1084. The base 1070, skirt 1076, spike 1080 and connector 1086 may be formed (e.g., molded) as a single unit out of polycarbonate, for example.

Unlike the embodiments of FIGS. 20-28, and more similar to the embodiments of FIGS. 1-18, the first subassembly 1064 does not include radially inwardly directed protrusions, projections or tabs. Instead, the skirt 1076 includes at least two slots 1090 that are parallel to the axis 1084 of the spike 1080. The slots 1090 have an open end 1092 and a closed end 1094. The slots 1090 receive therein radially outwardly projecting tabs 1096 of the second subassembly 1066, which tabs 1096 move along the slots 1090 to guide the first subassembly 1064 in a relatively axial motion relative to the vial 1060. The closed ends 1094 resist further motion of the tabs 1096 in the axial direction, thereby limiting the movement of the spike 1080 into the vial 1060 as will be explained. The slots 1090 include one or more projections or detents 1098 that depend inwardly into the slot 1090. The detents 1098 are formed to permit the tabs 1096 to advance into the open ends 1092 and past the detents 1098 during assembly of the vial adapter 1062, but then to resist separation of the first and second subassemblies 1064, 1066 thereafter with a surface of the tabs 1096 abutting the detents 1098.

In assembly, the spring 1068 is disposed in the between the first and second subassemblies 1064, 1066. In particular, a first end 1100 of the spring 1068 abuts an edge 1102 of the skirt 1076, while a second end 1104 of the spring 1068 abuts a radially outwardly depending shoulder 1106 of the second subassembly 1066. With the tabs 1096 received in the slots 1090 and separation of the first and second subassemblies 1064, 1066 resisted by the cooperation of the tabs 1096 and the detents 1098, the spring 1068 may be under a certain amount of initial compression, However, this need not be the case according to all embodiments.

In use, the entire vial adapter 1062 is fitted over the vial 1060 and brought axially downwardly into contact with the vial 1060. The spike 1080 advances into a stopper 1110 associated with the vial 1060 (see FIG. 30). In doing so, the first subassembly 1064 also advances axially toward the second subassembly 1066, thereby compressing the spring 1068 between the shoulder 1106 and edge 1102. The tabs 1096 also travel along the slots 1090 toward the closed ends 1094. The first assembly 1064 may cease its motion when the side 1072 of the base comes into contact with an upper surface 1112 of the vial 1060. Alternatively, the first assembly 1064 may cease its axial motion upon full compression of the spring 1068, for example.

With the user grasping the second subassembly 1066, the user releases the first subassembly 1064. The biasing or return force of the spring 1068 acts on the first subassembly 1064 through the interaction of the first end 1100 of the spring 1068 and the edge 1102 of the skirt 1076 (see FIG. 31). This causes the first subassembly 1064 to move axially away from the second subassembly 1066 and the vial 1060, thus withdrawing the spike 1080 relative to the stopper 1110.

Having thus discussed a number of embodiments wherein the withdrawal of a spike from a vial is controlled automatically and the force required to effect the withdrawal is provided through a mechanical device separate and apart from the user, the discussion will now turn to a number of embodiments of a vial adapter wherein the withdrawal of the spike relative to the vial is still controlled (or limited) automatically (i.e., by the device), but the force is provided by the user directly.

In this regard, a vial 1120 and a vial adapter 1122 are illustrated in FIGS. 32-34. The vial adapter 1122, similar to those explained above, includes more than one subassembly. In particular, the vial adapter 1122 includes a first subassembly 1124 and a second subassembly 1126. The first and second subassemblies 1124, 1126 cooperate to facilitate removal of a spike associated with the first subassembly 1124 a predetermined distance from the vial 1120 associated with the second subassembly 1126.

The first subassembly 1124 includes a base 1130 having first and second opposing sides 1132, 1134 (see FIGS. 33 and 34 as well). A tubular skirt 1136 may depend from the first side 1132 of the base 1130, the tubular skirt 1136 bounding a space 1138 to receive the vial 1120. A spike 1140 may depend from the first side 1132 of the base 1130 into the space 1138. The spike 1140 may have a longitudinal axis 1142 and a spike passageway 1144 (see FIGS. 33 and 34). The first subassembly 1124 may also include a connector 1146 disposed on the second side 1134 of the base 1130, the connector 1146 having a connector passageway 1148 that is in fluid communication with the spike passageway 1144 (see FIGS. 33 and 34). The base 1030, skirt 1036, spike 1040 and connector 1046 may be formed (e.g., molded) as a single unit out of polycarbonate, for example.

The skirt 1136 has a first cylindrical region 1150 and a second cylindrical region 1152 joined at a step or shoulder 1154. The first cylindrical region 1150 accepts an end of the vial 1120, while the second cylindrical region 1152 accepts the vial 1120 and the second subassembly 1126 fitted about the vial 1120. In particular the second cylindrical region 1126 has an inner surface 1156 that cooperates with a surface 1158 of the second subassembly 1126 to resist or limit the withdrawal of the spike 1140 from the vial 1120.

With reference to FIG. 32, the second subassembly 1126 includes a first arcuate section 1170 and a second arcuate section 1172. The first and second sections 1170, 1172 are joined at first ends 1174, 1176 by a hinge 1178, a living hinge as illustrated. The hinge 1178 may be sized so as to provide a biasing force to the first and second sections 1170, 1172 as well, to urge the surfaces 1156, 1158 of the first and second subassemblies 1124, 1126 into engagement with each other. Second ends 1180, 1182 of the first and second sections 1170, 1172 may also be joined together once the second subassembly 1126 is fitted to the vial 1120, preferably in a neck region 1184 of the vial 1120 (see FIG. 32). To this end the second end 1180 of the first section 1170 is provided with a tongue 1186 that is received and secured within a groove 1188 in the second end 1182 of the second section 1172.

As seen in FIGS. 33 and 34, the second subassembly 1126 is fitted onto the neck 1184 of the vial 1102, with the tongue 1186 received within the groove 1188 to secure the subassembly 1126 to the vial 1120. The first subassembly 1124 is then advanced along the axis 1142 in the direction of the vial 1120. The spike 1140 advances into a stopper 1190 until such time as a surface 1192 of the vial abuts or nearly abuts the side 1132 of the base 1130. At the same time, the second subassembly 1126 is received within the second cylindrical region 1152 of the first subassembly 1124. To withdraw the spike 1140 from the stopper 1190, a force or pair of forces is applied to the vial 1120 and the first subassembly 1124. The surfaces 1156, 1158 oppose the withdrawal of the second subassembly 1126 from the first subassembly 1124, and thereby control the amount of withdrawal of the spike 1140 from the stopper 1190. In this regard, the inner surface 1156 of the region 1126 may be tapered radially inwardly to oppose the withdrawal of the second subassembly 1126 from the first subassembly 1124; in addition, while not illustrated, an radially inwardly depending rim or lip may depend from the inner surface 1156 at any point along the surface 1156 or at the open end of the second cylindrical region 1126 to cooperated with the second subassembly (or collar) 1126 to oppose the withdrawal of the second subassembly 1126 from the first subassembly 1124.

Figure 37:
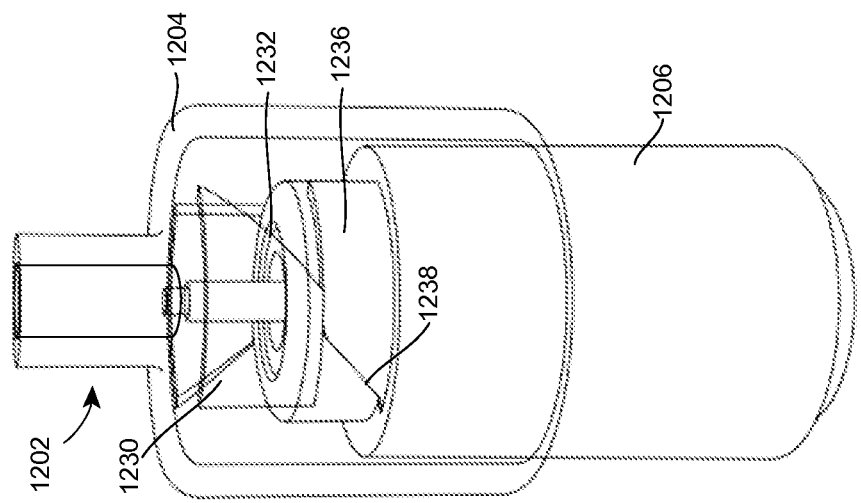
FIG. 37 is a perspective view of the vial adapter of FIG. 35 in a second position relative to the vial.
Figure 36:
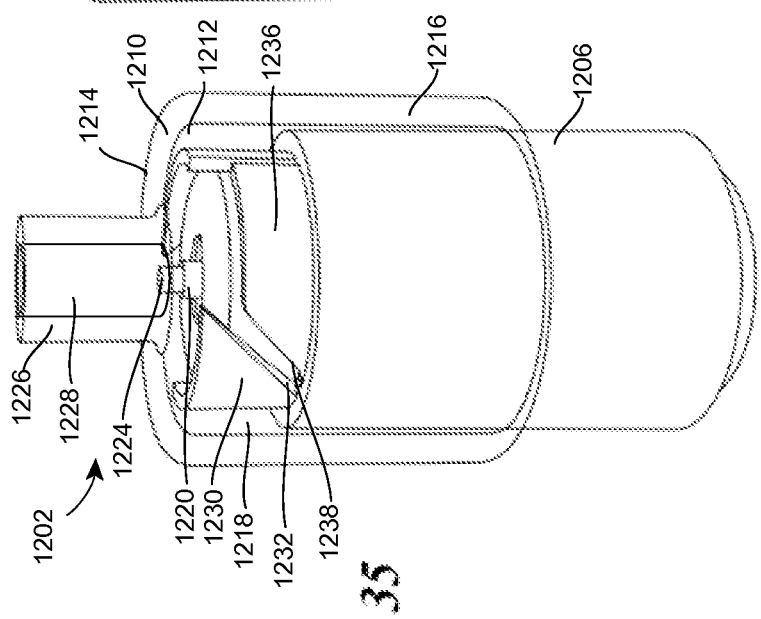
FIG. 36 is a perspective view of the vial adapter of FIG. 35 in a first position relative to the vial.
Figure 35:
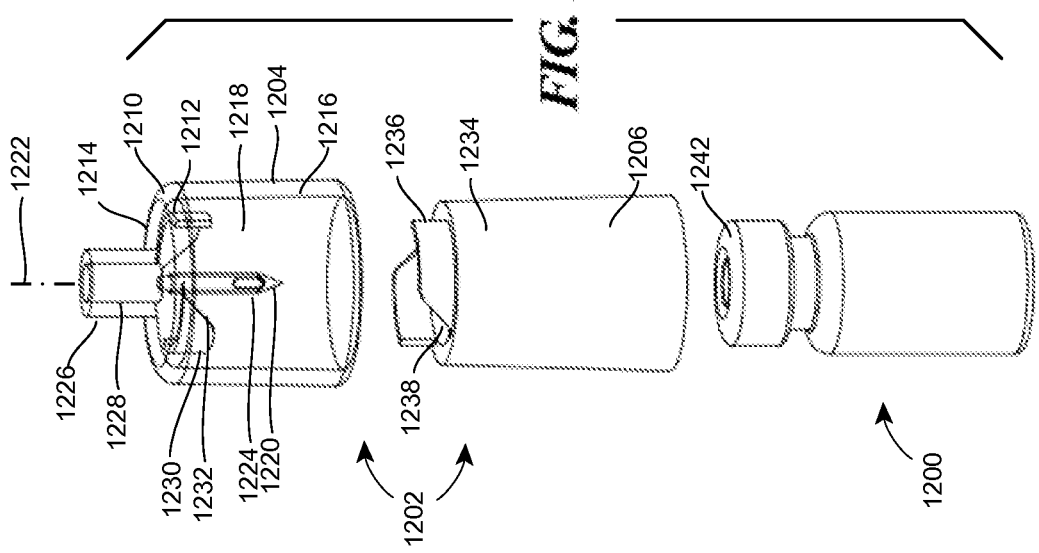
FIG. 35 is an exploded view of a fifth alternative vial adapter configured to address the trapped residual volume of FIG. 19 in combination with a vial.

It will be recognized that the cooperation of the surfaces 1156, 1158 of the embodiment of FIGS. 32-34 may not be sufficiently controlled for all uses. However, the concept of a pair of surfaces moving in contact with each other under a force applied by the user so as to control the withdrawal of a spike from a vial is common throughout the embodiments of FIGS. 32-40. Turning first to FIGS. 35-37, a vial 1200 and a vial adapter 1202 are illustrated. The vial adapter 1202 includes a first subassembly 1204 and a second subassembly 1206 that cooperate with each other as explained in greater detail below.

The first subassembly 1204 includes a base 1210 having first and second opposing sides 1212, 1214 (see FIGS. 36 and 37 as well). A tubular skirt 1216 may depend from the first side 1212 of the base 1210, the tubular skirt 1216 bounding a space 1218 to receive the vial 1200. A spike 1220 may depend from the first side 1212 of the base 1210 into the space 1218 (see FIG. 35). The spike 1220 may have a longitudinal axis 1222 and a spike passageway 1224. The first subassembly 1204 may also include a connector 1226 disposed on the second side 1214 of the base 1210, the connector 1226 having a connector passageway 1228 that is in fluid communication with the spike passageway 1224. The base 1210, skirt 1216, spike 1220 and connector 1226 may be formed (e.g., molded) as a single unit out of polycarbonate, for example.

The first subassembly 1204 also includes a shoulder 1230 disposed radially inwardly of the skirt 1216. The shoulder 1230 defines an arcuate, angled camming surface 1232. The second subassembly 1206 includes a hollow, cylindrical surface 1234 with a first end 1236 having an arcuate, angled camming surface 1238. The camming surfaces 1232, 1238 mate to control the relative motion of the first and second subassemblies 1204, 1206 to as to control the withdrawal of the spike 1220 from a stopper 1240 of the vial 1200 as follows.

In use, the combination of the first and second subassemblies 1204, 1206 is advanced axially toward the vial 1200. The spike 1220 advances into the stopper of the vial (similar to that illustrated in FIGS. 21 and 22, for example), and the vial adapter 1202 advances until a surface 1242 of the vial 1200 abuts or nearly abuts the side 1212 of the base 210 of the vial adapter. The surface 1232 of the shoulder 1230 faces the surface 1232 of the second subassembly 1206 at this time.

At this point, the spike 1220 may be withdrawn from the stopper by rotating the first subassembly 1204 and/or the second subassembly 1206 relative to each other. As the first and second subassemblies 1204, 1206 rotate relative to each other, the surfaces 1232, 1238 abut against each other and then move along each other, causing the first subassembly 1204 to withdraw away from the second subassembly 1206 (compare FIG. 36 with FIG. 37). With sufficient rotational motion, the surface 1232 moves along the surface 1238 until such time as the shoulder 1230 is received above the end 1238 of the second subassembly 1206. At this point, the spike 1220 has been withdrawn from the vial 1200 the predetermined about to prevent formation of a trapped residual volume.

The embodiment of FIGS. 38-40 may be viewed as a continuation of the embodiment of FIGS. 35-37. That is, the camming surfaces 1232, 1238 may be viewed as a single thread, while the embodiment of FIGS. 38-40 involves multiple threads. As a consequence, the variant of FIGS. 38-40 may provide a more secure connection between first and second subassemblies, as well as a finer degree of control of the separation of the first and second subassemblies relative to each other to effectuate the separation of a spike from a stopper associated with a vial.

FIG. 38 illustrates the combination of a vial 1260 and a vial adapter 1262. As mentioned above, the vial adapter 1262 includes a first subassembly 1264 and a second subassembly 1266.

The first subassembly 1264 includes a base 1270 having first and second opposing sides 1272, 1274 (see FIGS. 39 and 40 as well). A tubular skirt 1276 may depend from the first side 1272 of the base 1270, the tubular skirt 1276 bounding a space 1278 to receive the vial 1260. A spike 1280 may depend from the first side 1272 of the base 1270 into the space 1278. The spike 1280 may have a longitudinal axis 1282 and a spike passageway 1284. The first subassembly 1264 may also include a connector 1286 disposed on the second side 1274 of the base 1270, the connector 1286 having a connector passageway 1288 that is in fluid communication with the spike passageway 1274. The base 1270, skirt 1276, spike 1280 and connector 1286 may be formed (e.g., molded) as a single unit out of polycarbonate, for example.

The skirt 1276 also has an inner surface 1290 on which is formed at least one thread 1292. The at least one thread 1292 may be a continuous thread, or as illustrated, the at least one thread 1292 may include one or more discrete and separate thread segments. The at least one thread 1292 mates with a similar thread 1294 formed on an outer surface 1296 of a hollow, cylindrical housing 1298 that at least in part defines the second subassembly 1266. The threads 1292, 1294 operate to withdraw the spike 1280 in a controlled fashion according to the following method of operation.

In use, the combination of the first and second subassemblies 1264, 1266 is advanced axially toward the vial 1260. The spike 1280 advances into a stopper of the vial 1260, and the vial adapter 1262 advances until a surface 1302 of the vial 1260 abuts or nearly abuts the side 1272 of the base 1270 of the vial adapter 1262. At this point, the spike 1280 may be withdrawn from the stopper 1300 by rotating the first subassembly 1264 and/or the second subassembly 1266 relative to each other. As the first and second subassemblies 1264, 1266 rotate relative to each other, the threads 1292, 1294 move one within the other, causing the first subassembly 1264 to withdraw away from the second subassembly 1266. With sufficient rotational motion, the threads 1292, 1294 move one within the other until such time as the threads 1292 abut an end 1304 of the thread 1294. At this point, the spike 1280 has been withdrawn from the vial 1200 the predetermined about to prevent formation of a trapped residual volume.

A still further alternative to the camming or threaded variants of FIGS. 35-40 is illustrated in FIGS. 41-43. FIG. 41 illustrates a system including a vial 1320 and a vial adapter 1322 (which may also be referred to as a vial adapter assembly) prior to the vial adapter 1322 being attached to the vial 1320. As to the structure of the vial adapter 1322, the vial adapter 1322 includes two subassemblies 1324, 1326.

The first subassembly 1324 includes the tubular skirt 1330 that depends from a first end 1332 to a second end 1334, the tubular skirt 1330 bounding a space 1336 to receive the vial 1330. Attached to the skirt 1330 are a plurality of inwardly, radially directed protrusions, projections or tabs 1338. The tabs 1338 each have a surface 1340 that cooperates with a surface 1342 of the vial 1320 to prevent separation of the vial adapter 1322 from the vial 1320.

The tubular skirt 1330 also includes flaps 1350 defined in the skirt 1330 by a U-shaped slot in a wall of the skirt 1330. While the present illustration includes three such flaps 1350, it will be recognized that a lesser number (e.g., two) or a greater number (e.g., four) may be used instead. Each of the flaps 1350 includes a radially inwardly directed wedge 1352 with a surface 1354. The cooperation of the wedge 1352 with the other structures of the vial adapter 1322 and its role in the operation of the withdrawal of an associated spike will be discussed in greater detail below.

The second subassembly 1326 includes a base 1360 with a first side 1362 and a second side 1364, a spike 1366 (with an axis 1368) depending from the first side 1362 and a connector 1370 depend from the second side 1364. The spike 1366 and the connector 1370 may both have passageways 1372, 1374 (see FIG. 41). The base 1360 may also have an inclined edge 1376 that will cooperate with the wedge surface 1354 as explained below. The base 1360, spike 1366, and connector 1370 may be formed (e.g., molded) as a single unit out of polycarbonate, for example.

The second subassembly 1326, or at least the base 1360 of the second subassembly 1326, is received within the first subassembly 1324 in the space 1336. In particular, the base 1360 may be disposed in the space 1336 between the first end 1332 of the skirt 1330 and the wedges 1352 of the flaps 1350. As such, the first and second subassemblies 1324, 1326 are associated with each other for use relative to the vial 1320 as a single unit.

In operation, the vial adapter 1322 is advanced in the direction of the vial 1320 so that the spike 1366 advances into a stopper associated with the vial 1320 (similar to that illustrated in FIGS. 21 and 22, for example). With the application of force to both the subassemblies 1324, 1326 in the direction of the vial 1320, the spike 1366 further advances into the stopper 1380 and the tab 1338 is received in a neck 1382 of the vial 1320 such that the surfaces 1340, 1342 abut each other to resist separation of the first subassembly 1324 from the vial 1320. As further force is applied to the second subassembly 1326, the spike continues to advance into the stopper 1380 until the surface 1362 abuts a surface 1384 of the vial 1320.

As the second assembly 1326 advances in the direction of the vial 1320, the edge 1376 of the base 1360 cooperates with the wedges 1352 (an in particular the surfaces 1354) to force the wedges 1352 radially outward. The surface 1384 of the vial 1320 may also force the wedges radially outward as well. To withdraw the spike 1366 from the stopper 1380, a radially inward force is applied to the flaps 1350, and thus to the associated wedges 1352 (see FIG. 43). As the wedges 1352 move radially inward, the surfaces 1354 and the edge 1376 cooperate, causing the wedge 1352 to move radially inward between the surface 1384 and the side 1362 of the base 1360. As the wedges 1352 continue to move radially inward, the base 1360 (and thus the spike 1366) move away from the vial 1320 a distance determined by the thickness of the wedges 1352.

It will be recognized that a variant of a system including a vial 1400 and a vial adapter 1402 of FIGS. 41-43 is illustrated in FIGS. 44-46. In distinction to the embodiment of FIGS. 41-43, the vial adapter 1420 of FIGS. 44-46 may be applied to the vial 1400 as two subassemblies 1404, 1406, but then the two subassemblies 1404, 1406 may be used in concert once a spike is driven into a stopper of the vial 1400 to withdraw the spike relative to the stopper (and the vial 1400).

The first subassembly 1404 includes the tubular skirt 1410 that depends from a first end 1412 to a second end 1414, the tubular skirt 1410 bounding a space 1416 to receive the vial 1400. Attached to the skirt 1410 are a plurality of inwardly, radially directed protrusions, projections or tabs 1418 (see FIGS. 45 and 46). The tabs 1418 each depend from a flap 1420 defined in the skirt 1410 by a U-shaped slot in the wall of the skirt 1410. Each tab 1418 may have a surface 1422 that cooperates with a surface 1424 of the vial 1400 to prevent separation of the vial adapter 1402 from the vial 1400.

The tubular skirt 1410 also includes flaps 1426 defined in the skirt 1410 by a U-shaped slot in a wall of the skirt 1410. While the present illustration includes three such flaps 1426, it will be recognized that a lesser number (e.g., two) or a greater number (e.g., four) may be used instead. Each of the flaps 1426 includes a radially inwardly directed wedge 1428 with a surface 1430. The cooperation of the wedge 1428 with the other structures of the vial adapter 1402 and its role in the operation of the withdrawal of an associated spike will be discussed in greater detail below.

The second subassembly 1406 includes a base 1440 with a first side 1442 (see FIGS. 45 and 46) and a second side 1444, a spike 1446 with an axis 1448 depending from the first side 1442 and a connector 1450 depend from the second side 1444. The spike 1446 and the connector 1450 may both have passageways 1452, 1454. The base 1440 may also have an inclined edge 1456 that will cooperate with the wedge surface 1430 as explained below. The base 1440, spike 1446, and connector 1450 may be formed (e.g., molded) as a single unit out of polycarbonate, for example.

In operation, the vial 1400 is disposed in the skirt 1410 such that the tabs 1418 are received in a neck 1458 of the vial 1400 such that the surfaces 1422, 1424 abut each other to resist separation of the first subassembly 1404 from the vial 1400. The second subassembly 1406 is then disposed in the end 1414 of the skirt 1410 and advanced in the direction of the vial 1400 so that the spike 1446 advances into a stopper 1460 associated with the vial 1400. With the application of further force to the subassembly 1406 in the direction of the vial 1400, the spike 1446 further advances into the stopper 1460 until the surface 1442 abuts or nearly abuts a surface 1462 of the vial 1400 (see FIG. 45).

As the second assembly 1406 advances in the direction of the vial 1400, the edge 1456 of the base 1440 cooperates with the wedges 1438 to force them radially outward. To withdraw the spike 1446 from the stopper 1460, a radially inward force is applied to the flaps 1426, and thus to the associated wedges 1428. As the wedges 1428 move radially inward, the surfaces 1430 and the edge 1456 cooperate, causing the wedge 1428 to move radially inward under the edge 1456 of the base 1440 (see FIG. 46). As the wedges 1428 continue to moves radially inward, the base 1440 (and thus the spike 1446) move away from the vial 1400 a distance determined by the thickness of the wedges 1428.

As still further embodiment of a vial 1480 and vial adapter 1482 is illustrated in FIGS. 47-49. The vial adapter 1482 includes a base 1490 having first and second opposing sides 1492, 1494. A tubular skirt 1496 may depend from the first side 1492 of the base 1490, the tubular skirt 1496 bounding a space 1498 to receive the vial 1480. A spike 1500 may depend from the first side 1492 of the base 1490 into the space 1498. The spike 1500 may have a longitudinal axis 1502 and a spike passageway 1504 (see FIG. 47). The vial adapter 1492 may also include a connector 1506 disposed on the second side 1494 of the base 1490, the connector 1506 having a connector passageway 1508 that is in fluid communication with the spike passageway 1504. The base 1490, skirt 1496, spike 1500 and connector 1506 may be formed (e.g., molded) as a single unit out of polycarbonate, for example.

The vial adapter 1482 also includes a plurality of inwardly, radially directed protrusions, projections or tabs 1510. The tabs 1510 each have a surface 1512 that cooperates with a surface 1514 of the vial 1480 to prevent separation of the vial adapter 1482 from the vial 1480. However, the distance between the side 1492 of the base 1490 and the surface 1512 of the tabs 1510 is such that the surfaces 1512, 1514 are not in abutment when the spike 1500 fully advances into the vial 1480 (i.e., the side 1492 abuts a surface 1516 of the vial 1480). See FIG. 48.

The vial adapter 1482 also includes a spacer 1520. The spacer 1520 cooperates with the vial 1480 and the remainder of the vial adapter 1480 to automatically withdraw the spike 1500 a predetermined distance from the vial 1480. As illustrated, the spacer 1520 has an annular base 1522 from which depend three legs 1524. It will be recognized that the number of legs 1524 may be less than or greater than the number illustrated. As illustrated in FIG. 47, each of the legs 1524 is attached at a first end 1526 to the annular base 1522, and has a protrusion or hook 1528 at a second end 1530 thereof. The legs 1522 are received within holes or apertures 1532 formed in the base 1490. Once the protrusions 1528 are disposed through the holes 1532, the protrusions 1528 cooperate with the base 1490 (and in particular the side 1492 of the base 1490) to prevent the spacer 1520 from be separated from the base 1490, and hence the remainder of the vial adapter 1482.

The operation of the vial adapter 1482 is now discussed relative to the illustrations of FIGS. 48 and 49. Initially, the vial adapter 1492 is advanced in the direction of arrow A in FIG. 48 such that the spike 1500 comes in contact with a stopper of the vial 1480. As the vial adapter 1482 is advanced so that the spike 1500 advances into the stopper of the vial 1480, the ends 1430 of the legs 1524 of the spacer 1520 come into contact with the surface 1516 of the vial 1480. As such, further advancement of the vial adapter 1482 in the direction of the vial 1480 causes the remainder of the vial adapter 1482 to move relative to the spacer 1520, until such time as the side 1492 of the base 1490 nearly abuts the surface 1516 of the vial 1480.

To withdraw the spike 1500 relative to the stopper 1540 of the vial 1480, the skirt 1496 of the vial adapter 1482 is grasped and a force is applied upwardly to move the remainder of the vial adapter 1482 relative to the spacer 1520. At the same time, a downward force is applied to the spacer 1520 to keep the ends 1530 of the legs 1524 in contact with the surface 1516 of the vial 1480; preferably, this is done with the vial 1480 on a countertop, for example. As will be recognized, these forces will cause the remainder of the vial adapter 1482 to move relative to the spacer 1520 until the side 1494 abuts the base 1522 of the spacer 1520. The distance traveled by the spike 1500 will thus be determined, to some extent, by the length of the legs 1524 and the thickness of the base 1490. To prevent the entire vial adapter 1482 from being separated from the vial 1480 during this process, it is intended for the tabs 1510 to be spaced from the side 1492 of the base 1490 a distance approximately equal to the desired distance of travel (withdrawal) of the spike 1500. It will be recognized that the spacing between the tabs 1520 and the side 1492 of the base 1490 may be used to limit the travel of the spike 1500 such that the side 1494 will not abut the base 1522 of the spacer 1520.

As still further embodiment of the vial adapter is illustrated in FIGS. 50-53. This embodiment is similar to that of FIGS. 47-49 in that application of force to the parts of the vial adapter will cause withdrawal of a spike from a vial. However, unlike the adapter of FIGS. 47-49, the adapter of FIGS. 50-53 entirely surrounds the vial.

Figure 50:
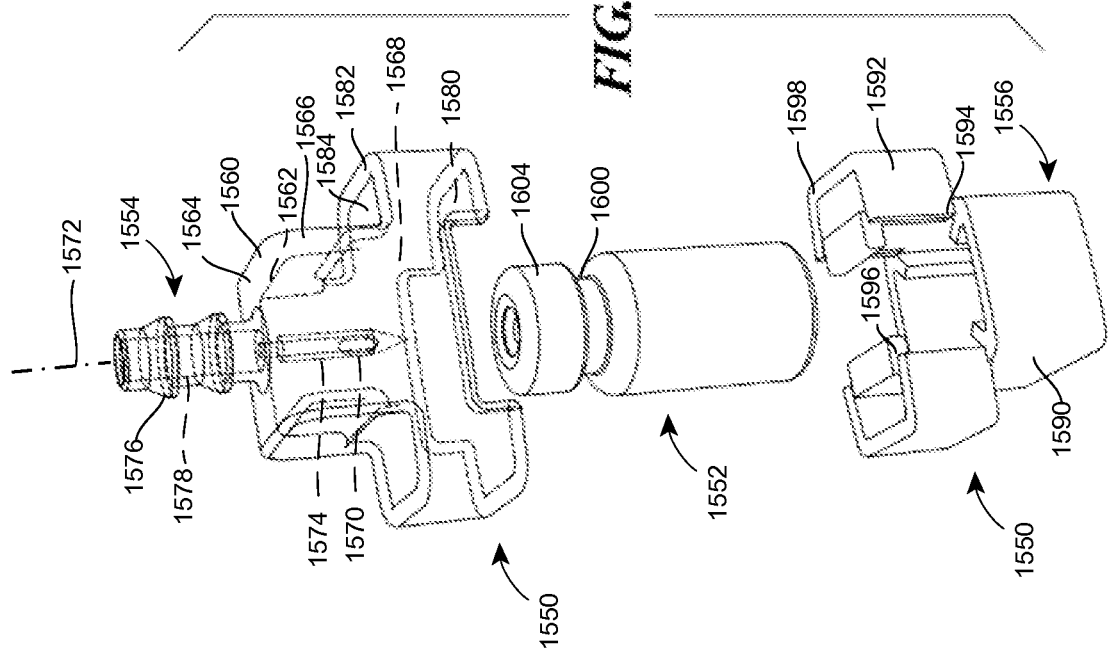
FIG. 50 is an exploded view of a tenth alternative vial adapter configured to address the trapped residual volume of FIG. 19 in combination with a vial.

Thus, a vial adapter 1550 and a vial 1552 are illustrated in FIG. 50. The vial adapter 1550 includes first and second subassemblies 1554, 1556. The first and second subassemblies 1554, 1556 may also be referred to as first and second housings in consideration of the fact that the vial adapter 1550 completely encloses the vial 1502.

Turning first to FIG. 50, the first subassembly or housing 1554 includes a base 1560 having first and second opposing sides 1562, 1564. A skirt 1566 may depend from the first side 1562 of the base 1560, the tubular skirt 1566 bounding a space 1568 to receive the vial 1502. A spike 1570 may depend from the first side 1562 of the base 1560 into the space 1568. The spike 1570 may have a longitudinal axis 1572 and a spike passageway 1574 (see also FIG. 51). The first subassembly 1556 may also include a connector 1576 disposed on the second side 1564 of the base 1560, the connector 1576 having a connector passageway 1578 that is in fluid communication with the spike passageway 1574 (again, see also FIG. 51). The base 1560, skirt 1566, spike 1570 and connector 1576 may be formed (e.g., molded) as a single unit out of polycarbonate, for example.

Figure 51:
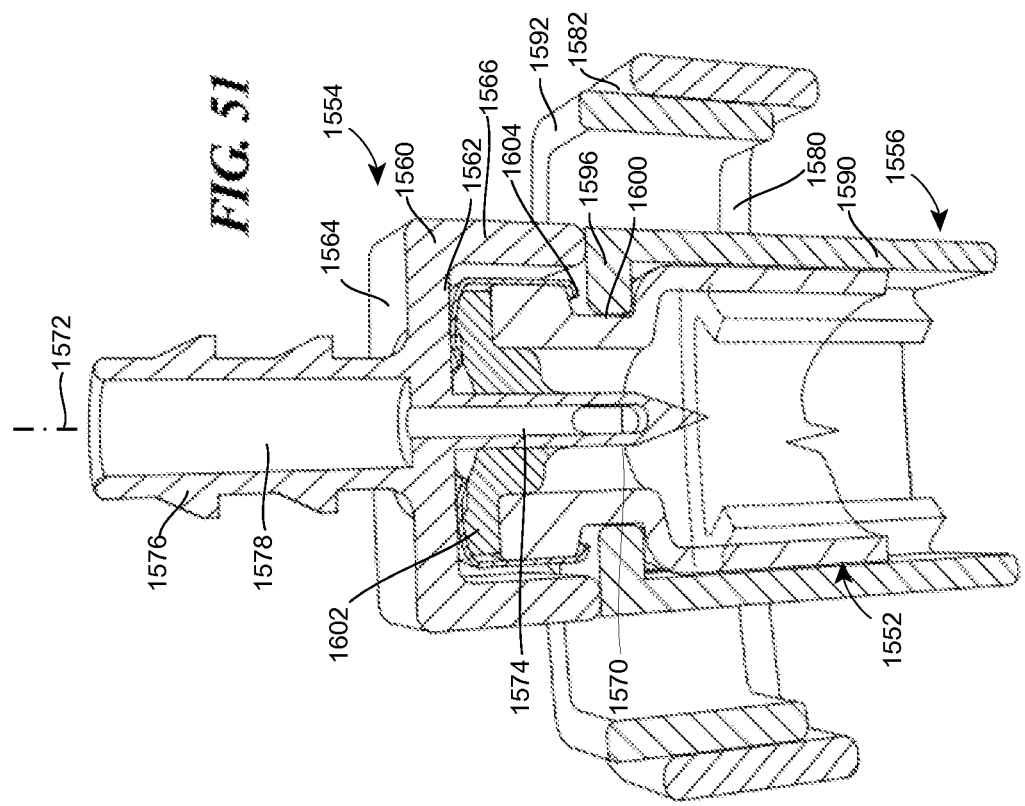
FIG. 51 is a cross-sectional view of the vial adapter of FIG. 50 in a first position relative to the vial.

The first subassembly 1554 also includes two side pockets 1580 (best seen in FIG. 51). Each side pocket 1580 is formed by a U-shaped wall 1582 attached to the skirt 1566 of the first subassembly 1554. The pockets 1580 are open along an axis parallel to the axis 1502 of the spike 1500, and thus form windows 1584 disposed along the sides of the skirt 1566 to either side of the spike 1570.

The second subassembly 1556 also includes a hollow skirt 1590 to receive the vial 1552. Attached to the sides of the skirt 1590 are two ears 1592. The ears 1592 are received within the pockets 1580 of the first subassembly 1554, and depend through the windows 1584 as explained in greater detail below. The ears 1592 are attached at a first end 1594 to the skirt 1590, and have tabs 1596 disposed radially inwardly at second ends 1598. The tabs 1596 are received within a neck 1600 of the vial 1552, so that the second subassembly 1556 and the vial 1552 are attached to each other so that they move as a single unit.

In operation, the vial 1552 is first attached to the second subassembly 1556 by forcing the vial into the skirt 1590 so that the tabs 1596 are received within the neck 1600 of the vial 1552 (see FIG. 51). With the vial 1552 thus mounted in the second subassembly 1556, the second subassembly 1156 is fitted into the first subassembly 1554 such that the ears 1592 are received within the pockets 1580 of the first subassembly 1554. The first and second subassemblies 1554, 1556 are then moved relative to each other such that the spike 1570 is moved in the direction of the vial 1552 so that the spike 1570 advances into a stopper 1602 of the vial 1552 (see FIG. 51). Motion of the first and second subassemblies 1554, 1556 relative to each other will cause at least a portion of the ears 1592 to depend from the windows 1584 of the first subassembly 1554 as the spike 1570 continues to be advanced into the stopper 1602. The motion of the subassemblies 1554, 1556 ceases with the side 1562 of the base 1560 abutting or nearly abutting a surface 1604 of the vial 1552 (see FIG. 51).

To withdraw the spike 1570 from the stopper 1602 the desired distance, opposing forces may be applied to upper surfaces 1606 of the ears 1592 and lower surfaces 1608 of the walls 1582 that define the pockets 1580 (see FIG. 52).

This force causes the first and second subassemblies 1554, 1556 to move relative to each other such that the spike 1570 associated with the first subassembly 1554 is withdrawn from the stopper 1602. The spike 1570 is withdrawn from the stopper 1602 a distance the depends on the distance the upper surface 1606 of the ears 1592 depend above upper surfaces 1610 of the walls 1582 that define the pockets 1580.

In the alternative to withdrawing a spike from a stopper of a vial to limit or prevent the formation of a trapped residual volume in the vial, the spike may be shaped so as to permit the spike and the material of the stopper to be advanced relative to each other without withdrawal of the spike from the stopper. FIGS. 54-61 illustrate at least two embodiments of such a vial adapter, both of which include a stopper that is formed to cause the stopper to move relative to the spike when the spike is rotated while being maintained a fixed distance relative to the vial. It will be recognized that these embodiments may be combined with those described above to define an embodiment wherein the spike is moved axially relative to a vial and rotated relative to the vial to cause the spike and the stopper to move relative to each other in accordance with the disclosure of the present embodiments. Such a further variant may be proposed, for example, to use the relative motion between spike and stopper caused by the rotational motion of the spike to limit the axial distance that the spike must traverse relative to the stopper.

Thus FIGS. 54-57 illustrate a first system including a vial 1620 and a vial adapter 1622 (which may also be referred to as a vial adapter assembly) prior to the vial adapter 1622 being attached to the vial 1620. The vial adapter 1622 includes two subassemblies 1624, 1626.

The first subassembly 1624 includes the tubular skirt 1630 that depends from a first end 1632 to a second end 1634, the tubular skirt 1630 bounding a space 1636 to receive the vial 1620. Attached to the skirt 1630 are a plurality of inwardly, radially directed protrusions, projections or tabs 1638. The tabs 1638 each have a surface 1640 that cooperates with a surface 1642 of the vial 1620 to prevent separation of the vial adapter 1622 from the vial 1620.

The second subassembly 1626 includes a base 1650 with a first side 1652 and a second side 1654, a spike 1656 depending from the first side 1652 and a connector 1658 depending from the second side 1654. The spike 1656 and the connector 1658 may both have passageways 1660, 1662 (see FIG. 57). The spike 1656 also has a thread 1664 formed on an external surface 1666 of the spike 1656 (see also FIG. 55). The use of the thread 1664 is explained in greater detail below. The base 1650, spike 1656, and connector 1658 may be formed (e.g., molded) as a single unit out of polycarbonate, for example.

In operation, the vial adapter 1622 is advanced in the direction of the vial 1620, causing the spike 1656 to advance into a stopper 1680 of the vial 1620 (see FIG. 57). The advancement of the vial adapter 1622 is continued until the tabs 1638 are received within a neck 1682 of the vial 1620, with the surfaces 1640, 1642 abutting. The side 1652 may also be abutting a surface 1684 of the vial 1620.

To move the stopper 1680, or at least a surface 1686 of the stopper 1680 to limit or eliminate a trapped residual volume, the first subassembly 1624 is rotated about an axis 1686 (see FIG. 54). The thread 1664 on the spike 1656 cooperates with the material of the stopper 1680 to cause the stopper 1680 to advance along the spike 1656, pulling a surface 1688 upwardly relative to the spike 1656. This relative motion causes the trapped residual volume to be limited or eliminated.

In the alternative to utilizing a two-part vial adapter where the parts of the vial adapter move relative to each other, a single-part vial adapter 1700 may be used, as is illustrated in FIGS. 58-61, with the vial 1702. The vial adapter 1700 includes a spike 1704 that is formed integrally (i.e., as a single piece) with the remainder of the vial adapter 1700. In particular, the spike 1704 has a internal thread (or groove) 1706 formed in an outer surface 1708 of the spike 1704. In use, the vial adapter 1700 is rotated such that the thread 1706 cooperates with the material of a stopper 1710 of the vial 1702 to move the material upwardly relative to the spike 1704 so as to return a surface 1712 of the stopper 1710 to a relaxed state. As a consequence, a trapped residual volume defined by the deflected surface 1712 is either limited or eliminated.

Figure 62:
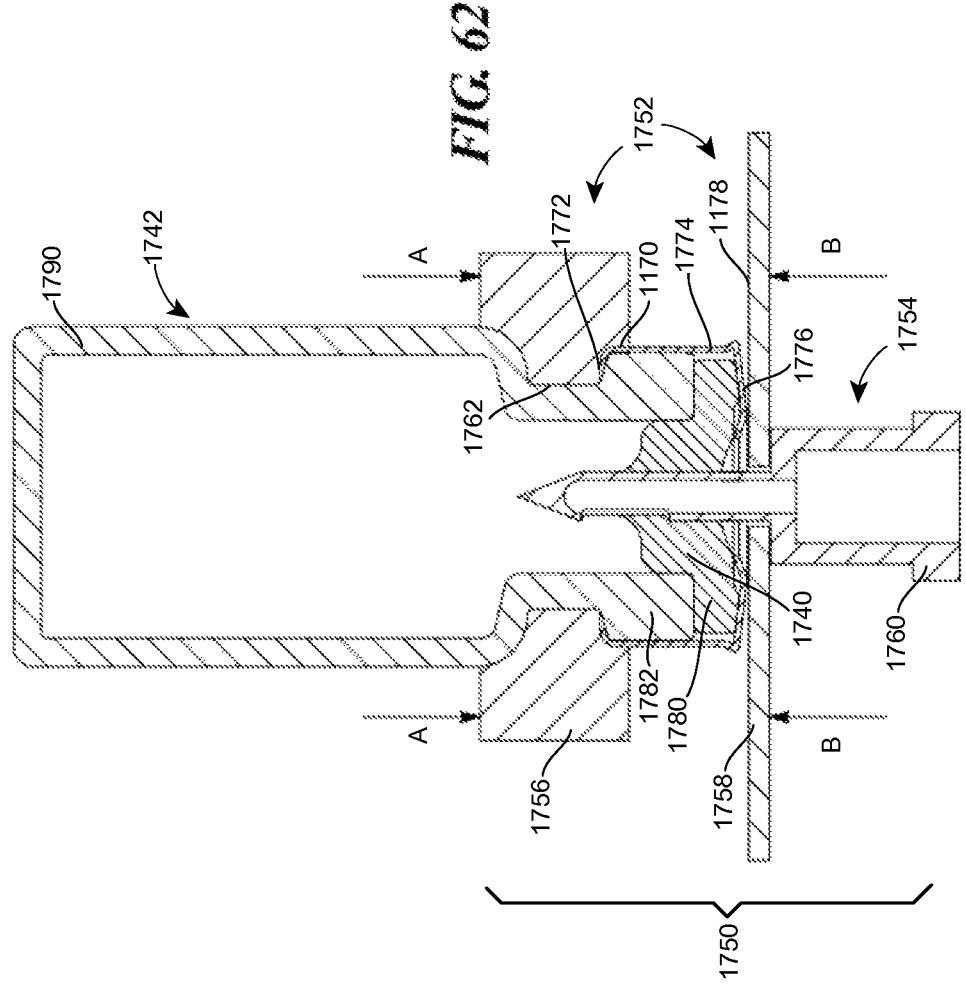
FIG. 62 is a cross-sectional view of a vial adapter to be used with a machine to facilitate retention of a stopper as a spike of the vial adapter is advanced into the stopper.

A still further embodiment of a vial adapter according to the present disclosure is illustrated in FIG. 62. This vial adapter is particularly well suited to address an issue that may arise as a spike associated with a vial adapter is advanced into a stopper associated with a vial, the stopper disposed over a passage in a neck of the vial to control access through the passage into the vial. Specifically, under certain loading conditions, the force applied to the stopper as the spike is advanced into the stopper will cause the stopper to move relative to the vial. As the spike advances further into the vial, a crimp ring disposed about the stopper and a rim disposed adjacent the neck of the vial to maintain the stopper fixed relative to the vial will be unable to resist the motion of the stopper. As a consequence, the stopper may move and become lodged within the passage in the neck of the vial. This can have a negative effect on the ability of the user to access the contents of the vial.

To limit the possibility of such movement of a stopper 1740 relative to the remainder of a vial 1742, a vial adapter 1750 as illustrated in FIG. 62 may be used. According to this embodiment, the vial adapter 1750 includes two subassemblies 1752, 1754 which may be physically separated from each other but indirectly attached to each other, through a frame or jig or a machine. The first subassembly 1752 includes a collar 1756; thus, this portion of the vial adapter 1750 is common to several of the embodiments illustrated above. The first subassembly 1752 also includes a plate 1758 that will be used in conjunction with the collar 1756 as explained in greater detail below. The second subassembly 1754 includes a spike 1760 that is intended to be advanced into the vial 1742 through a passage in the plate 1758, and in particular the stopper 1740 associated with the vial 1742. While the second subassembly 1754 may be moved manually by the user relative to the first subassembly 1752, it is intended for the second subassembly 1754 to be moved using a machine in an automated fashion.

Figure 64:
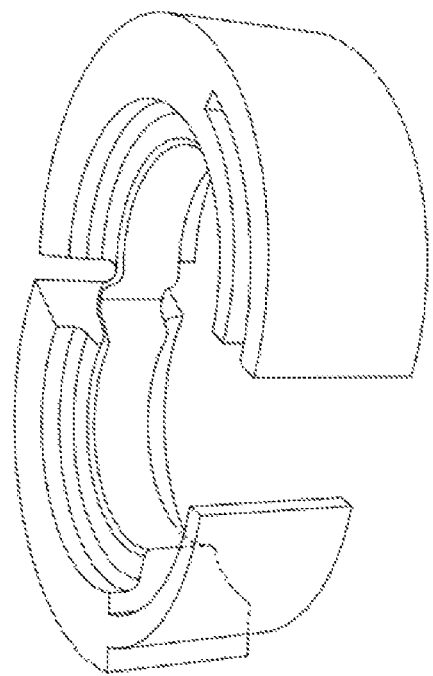
FIG. 64 is a perspective view of a second variant for a collar used in the vial adapter of FIG. 62.
Figure 63:
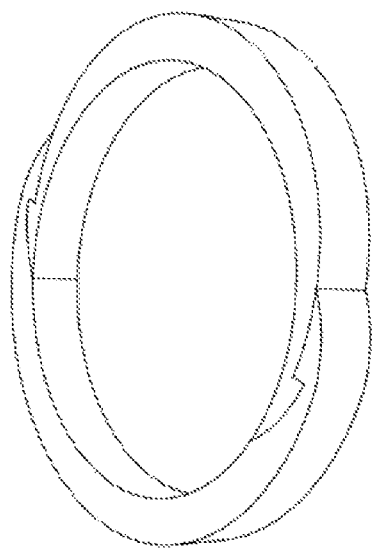
FIG. 63 is a perspective view of a first variant for a collar used in vial adapter of FIG. 62.

The collar 1756 may be similar to that illustrated in FIGS. 63 and 64, which is similar to that illustrated in FIGS. 17, 18 and 32, above. As illustrated in FIG. 63, the collar 1756 may include first and second C-shaped sections that are joined at opposing ends by one or more fasteners (such as the mating hooks, as illustrated). Alternatively, as illustrated in FIG. 64, the collar 1756 may include first and second sections that are joined by a hinge (such as a living hinge) at one pair of ends and by one or more fasteners (such as a tongue and groove fastener, as illustrated) at the other pair of ends. These sections are joined such that the collar 1756 is securely attached to the vial 1742 at a neck 1762 of the vial 1742.

In regard to materials, the second subassembly 1754, including the spike 1760, and the collar 1756 may be made of, for example, polymeric materials, such as plastics. Specifically, one exemplary material for the spike 1760 and the collar 1756 is polycarbonate, while another exemplary material for the collar 1756 is polypropylene. The plate 1758 may be made of metal, although it is also possible to use other materials as well.

In operation, a surface 1770 of the collar 1756 abuts a surface 1772 of a crimp ring 1774 associated with the vial 1742. As illustrated, an inner surface of the collar 1756 is shaped to match the contour of the crimp ring 1774, as well as the contour of a shoulder of the vial 1742, and thus is disposed to fill the neck 1762 of the vial 1742; this is an exemplary embodiment, and should not be viewed as a limiting feature of the collar 1756. An opposite surface 1776 of the crimp ring 1774 abuts a surface 1778 of the plate 1758. A force (represented by arrow A) is applied in a first direction to the collar 1756, while an opposing force (represented by arrow B) is applied in the opposite direction to or by the plate 1758. That is, it will be understood that the opposing force represented by arrow B may simply be a reactive force to the force represented by arrow A or may be a separate force applied to the plate 1758; it will also be recognized that the force could be applied to the plate 1758 with the collar 1756 held fixed, such that the force represented by arrow A may be a reactive force instead. These forces are transmitted by the collar 1756 and the plate 1758 to the crimp ring 1774, and from the crimp ring 1774 to a section 1780 of the stopper 1740 and an enlarged rim 1782 of the vial 1742 disposed adjacent the neck 1762. It is believed that the application of forces in this fashion will limit the movement of the stopper 1740 relative to the vial 1742 as the spike 1760 advances into the vial 1742 through the stopper 1740.

It should be noted that the application of forces in this fashion has a decided advantage over application of the forces to the plate 1758 and an opposing end 1790 of the vial 1742. With the forces applied as shown, with the collar 1756 transmitting force in the region of the stopper 1740, crimp ring 1774, and rim 1782, the forces are applied to a relatively thick section of the glass container that defines, in part, the vial 1740. Consequently, it is believed that the rim 1782 will be more resistant to breakage that the relatively thinner wall that defines the second end 1790 of the vial 1742. In fact, it is believed that if imperfections are formed in the wall of the container during fabrication, loading the forces at opposing ends of the vial 1742 is more likely to result in failure than if the loading occurs in the relatively thicker region of the rim 1782. Consequently, it is believed that the vial adapter 1750 has significant advantages over existing technology in regard to providing suitable forces to oppose movement of the stopper 1750 relative to the remainder of the vial 1742 while limiting the chances for failure of the vial 1742 under such loading.

As will be recognized, the vial adapters according to the present disclosure may have one or more advantages relative to conventional technology, any one or more of which may be present in a particular embodiment in accordance with the features of the present disclosure included in that embodiment.

For example, in those embodiments including the slot in the skirt, as illustrated herein, the slot may provide that a secure connection or attachment is formed between the vial adapter and vial, such that the adapter is less likely to separate from the vial in use, particularly if the adapter is intended to be used with the vial over a prolonged period. These embodiments may also provide a visual indication of that the connection between the vial adapter and vial has been formed, in that the cooperation between slot and tab may be visualized from the outside of the adapter. Moreover, where the slot includes a particular geometric shape along a region of the slot, the embodiment of the vial adapter may provide a visual and/or a tactile indication that a particular vial with a particular composition container therein has been used with an appropriately mating adapter.

In those embodiments including a biasing mechanism, such as the resilient pad, the degree to which the vial securely mates with the corresponding vial adapter may be enhanced. Further, the inclusion of a needleless or needle-free connector may permit the vial adapter according to the present invention to be used in a completely needleless or needle-free system, thereby diminishing the risks to the patient, the healthcare workers and the equipment. Additionally, embodiments may allow more consistent withdrawal of vial contents, when the vial is being emptied through the use of a pump, for example. While various embodiments relate to a needleless or needle-free connector for the vial adapter, this does not preclude other embodiments that might use a needle instead.

Other advantages not specifically listed herein may also be recognized as well.

We claim:

1. A system comprising:
    a vial having a neck with a passage in the neck and a rim disposed adjacent the neck, a stopper disposed over the passage in the neck of the vial to control access through the passage into the vial, and a crimp ring disposed about the stopper and the rim to maintain the stopper fixed relative to the vial;
    a vial adapter including:
        a collar securely attached to the vial at the neck of the vial and having a continuous inner circumferential surface engaging the neck of the vial, the collar for receiving one of a pair of opposing axial forces to limit the movement of the stopper relative to the vial,
        a plate for receiving another of the pair of axial opposing forces, the plate being axially spaced apart from the collar, and
        a surface of the crimp ring abutting a surface of the collar and an opposite surface of the crimp ring abutting a surface of the plate; and
    a spike configured to be advanced through a passage in the plate and penetrate the stopper after the collar is securely attached to the vial.

2. The system according to claim 1, wherein the collar comprises first and second C-shaped sections that are joined at opposing ends by one or more fasteners.

3. The system according to claim 2, wherein the one or more fasteners are mating hooks.

4. The system according to claim 1, wherein the collar comprises first and second sections joined by a hinge at one pair of ends and by one or more fasteners at another pair of ends.

5. The system according to claim 4, wherein the hinge is a living hinge and the one or more fasteners are a tongue and groove fastener.

6. The system according to claim 1, wherein the inner circumferential surface of the collar is shaped to match a contour of a shoulder defining the neck of the vial and a contour of an outer surface of the crimp ring such that the collar fills the neck.

7. A method of operating a system comprising:
    applying a force to a collar securely attached to a vial having a neck with a passage in the neck and a rim disposed adjacent the neck, a stopper disposed over the passage in the neck of the vial to control access through the passage into the vial, and a crimp ring disposed about the stopper and the rim to maintain the stopper fixed relative to the vial, the collar securely attached to vial at the neck of the vial; and applying an opposing axial force to a plate, the plate being axially spaced from the collar, a surface of the crimp ring abutting a surface of the collar and an opposite surface of the crimp ring abutting a surface of the plate.

8. The method of operating a system according to claim 7, further comprising advancing a spike into the stopper associated with the vial.

9. The method of operating a system of claim 7, a portion of the crimp ring being positioned between the stopper and the plate.

10. The method of operating a system according to claim 7, comprising advancing a needle through the stopper and into the vial while applying the force to the collar and applying the opposing force to the plate.

* * * * *

UNITED STATES PATENT AND TRADEMARK OFFICE
CERTIFICATE OF CORRECTION

PATENT NO. : 9,662,271 B2
APPLICATION NO. : 13/503508
DATED : May 30, 2017
INVENTOR(S) : Mark D. Holt et al.

It is certified that error appears in the above-identified patent and that said Letters Patent is hereby corrected as shown below:

In the Specification

At Column 8, Line 7, "there" should be -- their --.

At Column 15, Line 27, "etc" should be -- etc. --.

At Column 36, Line 7, "a internal" should be -- an internal --.

Signed and Sealed this
Twenty-fourth Day of April, 2018

Andrei Iancu
*Director of the United States Patent and Trademark Office*